United States Patent
Zeitels et al.

(10) Patent No.: US 12,070,195 B2
(45) Date of Patent: Aug. 27, 2024

(54) SYSTEMS AND METHODS FOR DESIGN AND 3-D FABRICATION OF LARYNGOSCOPES, PHARYNGOSCOPES, AND ORAL CAVITY RETRACTORS

(71) Applicant: Endocraft, LLC, Warwick, RI (US)

(72) Inventors: Steven Zeitels, Newton, MA (US); David Beaudet, Conway, MA (US)

(73) Assignee: Endocraft, LLC, Warwick, RI (US)

( * ) Notice: Subject to any disclaimer, the term of this patent is extended or adjusted under 35 U.S.C. 154(b) by 0 days.

(21) Appl. No.: 18/218,288

(22) Filed: Jul. 5, 2023

(65) Prior Publication Data
US 2023/0355087 A1 Nov. 9, 2023

Related U.S. Application Data

(63) Continuation of application No. 17/959,148, filed on Oct. 3, 2022.

(60) Provisional application No. 63/251,600, filed on Oct. 2, 2021.

(51) Int. Cl.
| | |
|---|---|
| *A61B 1/267* | (2006.01) |
| *A61B 1/24* | (2006.01) |
| *A61B 1/32* | (2006.01) |
| *B33Y 80/00* | (2015.01) |
| *A61B 1/06* | (2006.01) |
| *A61B 17/00* | (2006.01) |

(52) U.S. Cl.
CPC ............ *A61B 1/267* (2013.01); *A61B 1/24* (2013.01); *A61B 1/32* (2013.01); *B33Y 80/00* (2014.12); *A61B 1/0676* (2013.01); *A61B 2017/00526* (2013.01)

(58) Field of Classification Search
CPC . A61B 2017/00526; A61B 1/24; A61B 1/267; A61B 1/273; A61B 1/32; B33Y 80/00
See application file for complete search history.

(56) References Cited

U.S. PATENT DOCUMENTS

| | | |
|---|---|---|
| 4,306,547 A | 12/1981 | Lowell |
| 4,384,570 A | 5/1983 | Roberts |
| 4,527,553 A | 7/1985 | Upsher |

(Continued)

OTHER PUBLICATIONS

Huysamen Henry Wynand et al, "3D Printed Laryngoscope for Endotracheal Intubation", South African Journal of Industrial Engineering, [Online] vol. 31, No. 3, Nov. 11, 2020 (Nov. 11, 2020), pp. 209-217.

(Continued)

*Primary Examiner* — Larry E Waggle, Jr.
(74) *Attorney, Agent, or Firm* — Potomac Law Group, PLLC

(57) ABSTRACT

In one aspect, a method of redesigning a laryngoscope, a pharyngoscope, or an oral cavity retractor is disclosed, which includes generating a computerized 3-D model of a laryngoscope, pharyngoscope, or an oral cavity retractor, adjusting one or more parameters of the 3-D model to obtain a 3-D design of a laryngoscope, pharyngoscope, or oral cavity retractor that can provide a desired visual access to the upper aerodigestive tract of a patient or a group of patients, and fabricating a laryngoscope, pharyngoscope, or an oral cavity retractor based on said 3-D design using an additive manufacturing technique, such as 3-D printing.

20 Claims, 17 Drawing Sheets

(56) References Cited

U.S. PATENT DOCUMENTS

| | | | |
|---|---|---|---|
| 4,567,882 | A | 2/1986 | Heller |
| RE32,158 | E | 5/1986 | Vukovic |
| 4,947,829 | A | 8/1990 | Bullard |
| 4,947,896 | A | 8/1990 | Bartlett |
| 4,982,729 | A | 1/1991 | Wu |
| 5,261,392 | A | 11/1993 | Wu |
| 5,287,848 | A | 2/1994 | Cubb et al. |
| 5,758,456 | A | 6/1998 | Case |
| 5,800,344 | A | 9/1998 | Wood et al. |
| 5,817,005 | A | 10/1998 | Cohen |
| 5,893,830 | A | 4/1999 | Zeitels |
| 5,944,654 | A | 8/1999 | Crawford |
| 6,080,102 | A | 6/2000 | Konou et al. |
| 6,629,924 | B2 | 10/2003 | Aydelotte |
| 6,955,645 | B1 | 10/2005 | Zeitels |
| 10,499,802 | B1 | 12/2019 | Chen et al. |
| 10,582,836 | B1 | 3/2020 | Wu et al. |
| 2002/0022769 | A1 | 2/2002 | Smith et al. |
| 2002/0144340 | A1 | 10/2002 | Last |
| 2003/0015055 | A1 | 1/2003 | Mozingo et al. |
| 2018/0168730 | A1* | 6/2018 | Nazy .................. G16H 30/40 |

OTHER PUBLICATIONS

International Invitation to Pay Additional fees and Partial Search Report, PCT/US2022/045563, dated Jan. 20, 2023, 15 pages.
International Search Report and Written Opinion, PCT/US2022/045563, dated Mar. 14, 2023, 20 pages.

\* cited by examiner

SYSTEMS AND METHODS FOR DESIGN AND 3-D FABRICATION OF LARYNGOSCOPES, PHARYNGOSCOPES, AND ORAL CAVITY RETRACTORS

RELATED APPLICATIONS

This application is a continuation of U.S. application Ser. No. 17/959,148 filed on Oct. 3, 2022, which claims priority to and the benefit of Provisional Patent Application No. 63/251,600 filed on Oct. 2, 2021, which is herein incorporated by reference in its entirety.

TECHNICAL FIELD

The following disclosure relates to systems and methods for designing and fabricating unique laryngoscopes, pharyngoscopes, and oral cavity retractors and more particularly to such systems and methods that allow designing and fabricating individualized laryngoscopes, pharyngoscopes, and oral cavity retractors.

BACKGROUND

Examination of the larynx, pharynx, and oral cavity are done with varied forms of retractors, spatulas, and speculums. Since the larynx and pharynx are deeper in the upper aerodigestive tract than the oral cavity, the instruments to visualize and/or treat these anatomical regions are often referred to as laryngoscopes and pharyngoscopes. Consequently, laryngoscopy and pharyngoscopy are procedures in which a physician examines a patient's larynx or pharynx to provide access to the anatomical regions of interest. For example, a laryngoscope provides a surgeon with access to examine and perform surgery on the glottis (true vocal cords), supraglottis (epiglottis, aryepiglottic folds, and false vocal cords), and subglottis (cricoid region). Moreover, because of the complex disparate anatomy of the different anatomical subsites of the larynx and pharynx, a physician might employ a glottiscope, subglottiscope, supraglottiscope, or differing pharynx specula. During endoscopic minimally-invasive surgical procedures, the surgeon must have optimal visual access to the problematic area to perform precise operations. For example, a glottiscope should be designed to provide the greatest access possible to the vocal cords. Unfortunately, due to extreme anatomical variations between patients, a laryngoscope or pharyngoscope used on one patient may not provide optimal visual access to the desired anatomical structure when used on another patient. In addition, similar to many craftsmen who prefer select tools, surgeons often develop an affinity for selected laryngoscopes and pharyngoscopes due to prior training, ongoing familiarity, and habitual style rather than optimal functionality. These surgeons often prefer disparate attributes of different scopes, however, often they must choose a primary design preference and unavoidably forego secondary preferences.

SUMMARY

Aspects of the present disclosure address the above-referenced problems and/or others.

The present teachings generally provide methods and systems for designing and fabricating laryngoscopes, pharyngoscopes, and oral cavity retractors (herein collectively referred to individually as "a transoral instrument" or simply "an instrument" and in plural as "transoral instruments" or "instruments"). In some embodiments, the methods and systems disclosed herein can be utilized to redesign one or more components/segments of existing instruments to enhance their functionality while retaining advantageous attributes of other components/segments thereof. By way of example, the redesigned instruments can be fabricated using 3-D printing techniques, as discussed in more detail below.

By way of example, and as discussed in more detail below, computer modeling systems, such as Computer Aided Design tools, can be employed in accordance with the present teachings to design a laryngoscope, a pharyngoscope, or an oral cavity retractor, or redesign one or more components/segments of an existing laryngoscope, pharyngoscope or an oral cavity retractor so as to maximize the exposure of the upper aerodigestive tract cavities when used by a surgeon.

As discussed in more detail below, the methods for designing or redesigning according to the present teachings can be used to design and fabricate laryngoscopes, pharyngoscopes, and/or oral cavity retractors that can provide optimal visual access to a target anatomic site, (e.g., upper aerodigestive tract cavities), for an individual patient or a group of patients, (e.g., based on common anatomical features). In some embodiments, a three-dimensional model of the upper aerodigestive anatomy of a patient or a group of patients (herein also referred to as an anatomical profile) can be created using imaging data. In general, the anatomical features that can affect access to the aerodigestive tract can be used in the three-dimensional model. By way of example, and without limitation, such anatomical features can include, for example, three-dimensional contours of the airway lumen based on bone structures, e.g., jaw bones, teeth, cervical spine, as well as associated soft-tissue. Further, the rheology of soft tissues of the aerodigestive tract, such as the tongue, palate, and/or pharynx musculature, can also be employed in modeling the anatomical profile of the aerodigestive tract. For example, certain groups of individuals may have diminished tissue distensibility/pliability due to, radiation treatment and/or trauma, which can render it difficult to gain access to their aerodigestive cavities. By way of further example, the anatomical profile may include the three-dimensional profile of a patient's (or a group of patients') jaw-opening capacity, the size (e.g., the diameter) of the aerodigestive lumen, the anatomical soft-tissue structural conformation as well as the geometrical relationships between such anatomical structures.

In some embodiments, the instruments can be designed, or redesigned, in accordance with the present teachings for a group of patients that exhibit similar anatomical profiles of their aerodigestive tracts, or certain features thereof. For example, some patients with Down syndrome may have relative macroglossia narrowing of the oropharyngeal inlet, which can interfere with gaining access to their aerodigestive tract. By integrating the 3-D reconstructed imaging from a CT-scan that delineates shape of the lumen, with the spatial relationships of the anatomic structures (junction of the glossotonsillar sulcus with the posterior floor of mouth) and soft tissue distensibility, the scope speculum can be suitably tailored and the optimal substrate material can be selected (e.g. titanium or cobalt chrome, etc.)

In other embodiments, the instruments can be designed, or redesigned, for patients who have undergone radiation treatment. As noted above, such patients may have soft tissues with diminished distensibility. For example, restricted jaw opening (trismus) along with stiff fibrotic tissue from prior radiotherapy will lead to laryngoscope shapes, contours, and narrowing requirements to accommodate these anatomic restrictions to positioning laryngoscopes, pharyngoscopes, or oral cavity retractors.

In some embodiments, the instruments can be designed, or redesigned, for a group of patients having one or more characteristics in common by obtaining anatomical profiles of a number of patients in that group and generating an average anatomical profile, e.g., by averaging various anatomical parameters, such as those disclosed herein.

In some embodiments, structural finite element analysis (FEA) can be utilized to analyze the response and tolerance of various components/segments of an instrument to stress and/or strain generated by a variety of simulated applied forces, such as those to which the instrument may be subjected during use. By way of example, such analysis can be used to assess different designs generated in accordance with the present teachings. For example, one or more design parameters that can affect visual access to the upper aerodigestive tracts can be varied over a range and the finite element analysis can be utilized to assess the response of various components/segments of the instrument to a set of applied forces for the different values of the design parameters. The analysis can then be employed to obtain design parameters that result in an instrument that permits optimal visual access to the aerodigestive tract while providing information regarding component(s)/segment(s) of the instrument that may require structural strengthening (reinforcement), e.g., by increasing the thickness of those component(s)/segment(s), without increasing wall thickness that would impede insertion and positioning of the scope. For example, thickened areas of the scope/speculum manufactured by 3-D printing can deposit additional materials on certain sections of the instrument and/or changing the material from which those component(s)/segment(s) are fabricated but not limit the instrument's functionality.

Subsequent to designing or redesigning an instrument according to the present teachings, e.g., via the use of imaging data and Computer Aided Design tools, the instrument can be fabricated using a variety of manufacturing techniques including, without limitation, additive manufacturing techniques, such as 3-D printing, CNC (computer numerical control) machining and/or selective laser sintering. It has been discovered that 3-D printing methods can be particularly advantageous for fabricating instruments designed in accordance with the present teachings. For example, 3-D printing techniques can be advantageously utilized for facile modification of certain structural components/segments of an instrument so as to provide structural reinforcement of those component(s)/segment(s). For example, 3-D printing can be used to deposit additional material on certain portions of the instrument to strengthen those portions, e.g., a region in proximity of a handle attachment element and a top plate of the instrument (speculum), as discussed in more detail below.

In some embodiments, the present teachings can be utilized to analyze existing laryngoscopes, pharyngoscopes, and/or oral cavity retractors to identify those features that attribute to optimal functioning of the instrument as well as those features, if any, that are sub-optimal. The present teachings can then be utilized to redesign the instrument so as to retain the optimal features while modifying the sub-optimal features to create new instruments based, for example, on individuals' anatomy, surgeon preference, and varying holding device or suspension gallows.

In one aspect, a method of redesigning a laryngoscope, a pharyngoscope, or an oral cavity retractor is disclosed, which includes generating a computerized 3-D model of a laryngoscope, a pharyngoscope, or an oral cavity retractor, adjusting one or more parameters of the 3-D model so as to obtain a 3-D design of the laryngoscope, the pharyngoscope or the oral cavity retractor that can provide a desired visual access to the upper aerodigestive tract of a patient or a group of patients, and fabricating a laryngoscope, a pharyngoscope or an oral cavity retractor based on said 3-D design using an additive manufacturing technique, such as 3-D printing. In some embodiments, certain structural features of the instrument that is being redesigned are retained while other features are modified (redesigned) so as to enhance the instrument's functionality, e.g., providing better visual access to a surgical site.

In some embodiments, the redesign of the instrument can be informed by 3-D modeling of the anatomy of the aerodigestive tract, including bone structures and soft tissues. In some embodiments, an anatomical profile of the aerodigestive tract of a patient or a group of patients can be acquired, and the computerized 3-D model can be generated based on that anatomical profile.

In some embodiments, a structural finite element analysis can be utilized to identify one or more segments or components associated with a 3-D design, generated as indicated above, that require structural strengthening/reinforcement. In such cases, the fabrication of the laryngoscope, the pharyngoscope, and/or the oral cavity retractor can include structurally configuring the identified one or more segments and/or components so as to provide structural reinforcement of those segments(s) and/or component(s). By way of example, those identified component(s)/segment(s) can be fabricated with a thickness, shape and/or composition such that those segment(s) and/or component(s) can withstand forces applied thereto during use.

In some embodiments, the present teachings relate to methods and systems for designing and fabricating a laryngoscope that includes a speculum having a base plate (herein also referred to as the bottom portion) and a top plate (herein also referred to as the top portion) that is coupled to the base plate to form a tubular speculum. In some cases, the structural strengthening of such a speculum can include adjusting the thickness, shape, and/or composition of a wall of the speculum or a portion thereof. By way of example, and without limitation, a portion of the upper plate in the proximity of a handle attachment element of the laryngoscope can be structurally reinforced to ensure that the speculum can withstand forces to which the junction of the handle attachment element and the top plate are exposed during use. By way of example, and without limitation, in some cases, the thickness of such portions can be increased relative to the other portions of the top plate by a factor in a range of about 10% to 100%, e.g., in a range of about 20% to about 80%, or in a range of about 30% to about 70%. Instead, or in addition, those portions can be made of a different material, e.g., a different metal, that can provide a more robust structural integrity. Further, the shape, e.g., the curvature, of those portions can be modified, e.g., the curvature can be reduced or increased, to render those portions less susceptible to structural failure when the laryngoscope is in use.

In one aspect, a method of producing a laryngoscope, a pharyngoscope, or an oral cavity retractor includes generating an anatomical profile of a patient, or an average anatomical profile associated with a patient group, and producing one or more components of a laryngoscope, pharyngoscope, or oral cavity retractor based on the anatomical profile. In some embodiments, the method further includes imaging of patients' upper aerodigestive tract, e.g., utilizing a variety of imaging techniques known in the art such as those disclosed herein, thereby generating image data and integrating the image data into the anatomical profile. The anatomical profile may include the three-dimensional profile of the patients' jaw-opening capacity, aerodigestive lumen, and anatomical soft-tissue structural conformation as well as a rheological assessment of the anatomic soft tissues peripheral to the airway lumen. The method may further include producing the component(s) of the laryngoscope, pharyngoscope, and/or oral cavity retractors with additive manufacturing techniques, such as three-dimensional (3D) printing. The components may comprise a metal, plastic, or composite material. In some embodiments, the method further includes determining one or more materials from which one or more components of the laryngoscope, the pharyngoscope, and/or the oral cavity retractor may be fabricated based on at least one of the anatomical profile, structural requirements, ease of maintenance and sterilization, and economy of production. The component may be a top plate of a speculum or a base plate thereof. In some embodiments, the method further includes determining a parameter of the component based on the anatomical profile and producing the component based on the determined parameter. By way of example, the parameter may include the length of any of the speculum components (i.e., the longitudinal distance between the proximal and the distal ends of these components), the inner diameter of the lumen of the speculum, the radius of curvature of the speculum, a tilt angle of a proximal portion of the base plate relative to the rest of the base plate, among others. Additionally, these geometric parameters and relationships can be suitably altered to accommodate a wide range of anatomic variations based on age, gender, prior injury, prior medical treatment such as radiotherapy, and a range of other comorbid factors.

In another aspect, a method for reconfiguring a laryngoscope, a pharyngoscope, or an oral cavity retractor is disclosed, which includes generating a 3-dimensional profile of the laryngoscope, the pharyngoscope, or the oral cavity retractor and using the 3-dimensional profile to generate a modified design of at least one or more segment(s)/component(s) of the laryngoscope, the pharyngoscope, or the oral cavity retractor, e.g., utilizing Computer Aided Design tools. By way of example, such a modified design may maintain the profile of the distal end of the instrument, but change one or more parameters of the instrument's proximal end, e.g., to improve visual access to a target site, especially if used with a surgical microscope. Altering the proximal portion of the laryngoscope may also be done to enhance the ability of an assistant to pass microscopic instruments to the surgeon by providing wider access to the lumen of the laryngoscope without obstructing the view of the microsurgical field of view. By way of another example, the modified design can relate to structurally reinforcing one or more segments of the instrument. Such structural reinforcement can be achieved, for example, by using a different material for the fabrication of that segment or increasing the thickness of that segment. In some embodiments, the modified design can be implemented using 3-dimensional (3-D) printing.

In other words, in embodiments, 3-D profiling of an existing instrument together with the use of Computer Aided Design for redesigning one or more portions of the instrument to generate a modified design, which can, for example, retain the profile and function of certain portions of the instrument while modifying other portions, and utilizing 3-D printing to implement the modified design can be used to fabricate an enhanced version of existing instruments.

In some embodiments, the redesign of an existing instrument according to the present teachings results in a modified instrument that can retain the primary structural and functional attributes of certain portions thereof while enhancing the structural and functional attributes of other portions.

The use of 3-D printing techniques, integrated with CAD tools, for the redesign of existing scopes, which are used, for example, in human endoscopic upper aerodigestive tract surgery, can provide certain advantages. By way of example, computerized analysis of structural stress and strain in various regions of an existing instrument can be utilized to identify regions of the instrument that are subjected to significant retraction forces. The thickness of such regions can be varied using, e.g., composite 3-D printing materials. Another advantage of the present teachings, and in particular using 3-D printing for fabricating oral instruments, is the ability to fabricate instruments on demand so that production of large quantities and maintenance of inventory can be fluidly scaled. In embodiments, the present teachings can facilitate the rapid and efficient design and/or redesign of transoral instruments and their fabrication using, e.g., additive techniques such as 3-D printing techniques.

In another aspect, a system for designing and fabricating laryngoscopes, pharyngoscopes, and oral cavity retractors includes a component-producing system, a computer-readable storage medium with computer readable program instructions, and a processor in communication with the computer-readable storage medium, wherein the processor is configured to execute computer readable program instructions stored in the computer-readable storage medium that can cause the processor to determine an anatomical profile of a patient, and in particular the anatomical profile of the patient's larynx, oropharynx, and oral cavity and send a signal to a component-producing system to produce the component based on the anatomical profile. In some embodiments, the processor is further configured to determine parameters of a component of a laryngoscope, a pharyngoscope, or an oral cavity retractor based on the anatomical profile and in response to receiving the signal, and the component-producing system is further configured to produce the component based on the parameters. The parameters may include, e.g., the length of a laryngoscope component, such as the length of any of the components of the speculum, such as the top plate and/or the base plate, the inner diameter of the lumen of the speculum, the radius of curvature of the speculum, a tilt angle of a proximal portion of the base plate relative to the rest of the base plate. In some embodiments, the configured processor is further configured to determine one or more design parameters of the instrument based on image data acquired for an individual patient or a group of patients. The component-producing system may be a 3D printer or other additive manufacturing equipment. The component may be a speculum, including a base plate and a top plate of a speculum. The material of the component may be metal, plastic, or a composite. In some embodiments, the configured processor is further configured to determine the material based on the anatomical profile, e.g., rheological information about the deformability of anatomic soft tissue of interest and/or other tissue. Although in many embodiments current stress/strain tolerance requires the use of a metal for forming a transoral instrument according to the present teachings, needs typically require metal, future constituent materials may have enough strength and be easier to print. Additionally, in embodiments of the present teachings, the use of stress/strain pressure profile of the instrument will enable more precise metal selection (e.g., titanium versus cobalt chrome) for fabrication of various components of an instrument, e.g., scope-speculum, as well as the selection of one or more geometrical parameters of those components, e.g., the thickness of the components.

In some embodiments, a three-dimensional reconstruction of the bone, cartilage, soft tissue, and aerodigestive lumen can be extracted from computerized axial tomography (CAT-Scan). These data can be integrated with structural features of soft tissues of the oral cavity, pharynx, and larynx, which can be critical for designing laryngoscopes, pharyngoscopes, and oral cavity retractors. Abnormal structural features of soft tissues are often manifested as local stiffening, Elastic and mechanical properties of soft tissues can be measured in vivo with enhanced spatial resolution using techniques such as micro-indentation, microelectromechanical (MEMS) based cantilever sensors, and optical catheters.

In yet another aspect, a method according to the present teachings includes analyzing one or more components of an existing laryngoscope, pharyngoscope, or oral-cavity retractor to determine one or more parameters of the component(s), herein also referred to as one or more actual parameters, determining one optimal parameter for at least one of the one or more component(s) of the instrument based on an anatomical profile, comparing the actual parameter of the component with the optimal parameter of the component to determine if the actual parameter is the same as the optimal parameter, and in response to determining the actual parameter is not the same as the optimal parameter, producing the component with the optimal parameter.

In yet another aspect, a method of fabricating a laryngoscope, a pharyngoscope, or an oral-cavity retractor having a speculum for use with an individual patient or a group of patients, includes collecting anatomical data regarding an individual patient's larynx, pharynx and/or oral cavity and obtaining one or more structural and/or compositional parameters of at least one of the components of such an instrument, e.g., the speculum or a component thereof (e.g., a base plate or a top plate of the speculum), by adjusting the parameters so as to obtain a desired visual access to a site of interest when using the instrument to visualize that site in the patient, and using the parameters to fabricate the component(s), e.g., the speculum or a component thereof (such as a base plate or a top plate). In some embodiments the step of obtaining said one or more structural and/or compositional parameters includes generating a computerized model of the laryngoscope, pharyngoscope, or oral cavity retractor. In some embodiments, the method further includes using the computerized model to adjust the one or more structural and/or compositional parameters.

In a related aspect, a method of redesigning a laryngoscope, a pharyngoscope, or an oral cavity retractor is disclosed, which includes generating a computerized 3-D model of a laryngoscope, pharyngoscope, or an oral cavity retractor, adjusting one or more parameters of the 3-D model to obtain a 3-D design of a laryngoscope, a pharyngoscope, or an oral cavity retractor that can provide a desired visual access to the upper aerodigestive tract of a patient or a group of patients, and fabricating a laryngoscope, a pharyngoscope, or an oral cavity retractor based on said 3-D design using an additive manufacturing technique, such as 3-D printing.

In some embodiments, the method can further include acquiring anatomical profile of a patient or a group of patients and generating said computerized 3-D design of the laryngoscope, pharyngoscope or the oral cavity retractor based on said anatomical profile.

In some embodiments, a structural finite element analysis can be employed to identify one or more segments or components associated with said 3-D design that require structural reinforcement. The fabrication step can then include structurally configuring the identified segment(s) or component(s) so as to provide structural reinforcement thereof. By way of example, the structural reinforcement of the identified segment(s) or component(s) can include adjusting any of a thickness, shape and/or composition of those segment(s) or component(s). The structural reinforcement can be designed such that the structurally reinforced segment(s) or component(s) can withstand the forces applied thereto when the instrument is used by a surgeon.

In some embodiments, the instrument can include a speculum having a top plate coupled to a base plate and the method includes adjusting at least one of a thickness, shape and composition of at least a portion of the top plate to provide structural reinforcement of that portion.

In some embodiments, the desired visual access can be characterized by a maximum tilt of a surgical microscope that is optically coupled to the instrument relative to a longitudinal axis of the instrument that can be used for viewing a surgical site of interest in the aerodigestive tract of a patient or a group of patients. For example, such a maximum tilt can be about 20 degrees, or about 30 degrees, or about 40 degrees.

Further understanding of various aspects of the present teachings can be obtained by reference to the following detailed description in conjunction with the associated drawings, which are described briefly below.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description taken in conjunction with the accompanying drawings in which.

DETAILED DESCRIPTION

Figure 1:
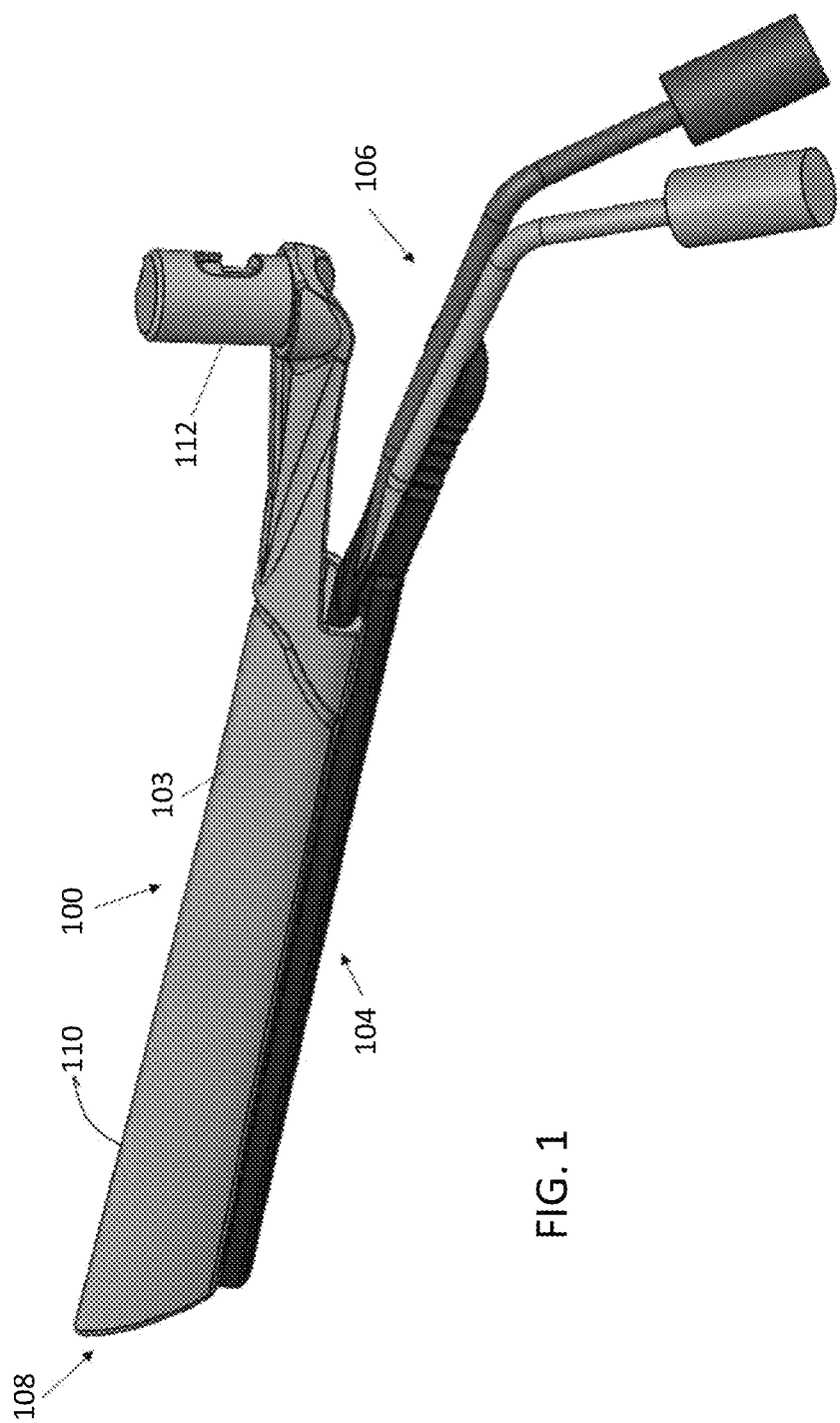
FIG. 1 illustrates a laryngoscope in accordance with an exemplary embodiment of the present disclosure.

In some aspects, the present disclosure generally relates to a system and method for designing or redesigning and fabricating laryngoscopes, pharyngoscopes and oral cavity retractors. A variety of these instruments have been used for over two centuries to examine and perform procedures on the oral cavity and throat. For example, a patient may undergo phonomicrosurgery to improve or maintain their voice. Various vocal-fold anomalies (e.g., polyps, nodules, cysts, granulomas, papilloma, epithelial dysplasia, cancerous growths, etc.) may cause the voice to become distorted. During phonomicrosurgery, a surgical microscope is used to view the anomalies. As such, this operation may be optimized by obtaining the widest glottal surgical field to expose vocal-fold anomalies. A laryngoscope with an internal lumen may be used to view a pathology or an anomaly during phonomicrosurgery. The purpose of a laryngoscope (as well as other instruments used during medical procedures involving the throat) is to provide the widest viewing and operating area possible to the surgeon. Unfortunately, a universally shaped laryngoscope may not provide the widest viewing and operating area possible to all patients due to anatomical variations, such as the jaw-opening capacity, size and/or shape of the mouth and throat, tissue distensibility (rheometry) diminishment from radiation or trauma among different individuals. Further, conventional laryngoscopes may not provide optimal visual access to a surgical site.

In some aspects, the present disclosure provides a system and method for designing and redesigning and producing a laryngoscope, a pharyngoscope, and an oral cavity retractor, that is specifically tailored to a patient's anatomy and an average anatomy of a group of patients. Providing a system and method for producing such an instrument that is individualized to a patient's or a group of patients' anatomy may provide the widest viewing and operating area as possible by exposing regions of the larynx, oropharynx, and oral cavity, for example, irrespective of age, gender, deformities, or prior surgery. In the following discussion, various aspects of the present teachings are described primarily in the context of designing and redesigning and fabricating laryngoscopes, but it should be understood that the present teachings can be applied to pharyngoscopes and oral cavity retractors.

In some aspects, the present disclosure relates to modifying a laryngoscope, pharyngoscope, or oral cavity retractor to improve its functionality. By way of example, a CAD tool can be utilized to redesign one or more components/segments of such an instrument and 3-D printing can be used to fabricate the redesigned instrument. For example, the redesign of the instrument can improve its functionality, e.g., by providing an enhanced field of view of the aerodigestive tracts to a surgeon, and/or strengthen certain components/segments of the instrument that experience significant stress/strain when used to view a patient's larynx, pharynx or oral cavity.

As used herein, the term "about" means plus or minus 25% of a numerical value. Therefore, about 200 μm means in the range of 75-125 μm.

As discussed in more detail below, in various embodiments, imaging techniques, such as diagnostic endoscopy (flexible and rigid) as well as varying forms of imaging such as computerized axial tomography, magnetic resonance imaging and/or rheometric measurements of head and neck soft tissues and/or jaw-opening capacity can be employed to provide a profile of the throat, and the profile can be utilized to fabricate an optimal laryngoscope for, e.g., for an individual patient or a group of patients, e.g., a laryngoscope that can provide a maximum visual access to the anatomical tissue of interest for an individual patient or a group of patients. For example, such imaging information from different imaging modalities can be integrated to obtain a specific anatomic profile that can be utilized to design and fabricate a speculum of a laryngoscope or a pharyngoscope that optimally exposes regions of the larynx, oropharynx, and oral cavity irrespective of age, gender, deformities, or prior surgery, etc.

For example, as discussed in more detail below, the anatomical information can be used to optimize the geometry of the speculum (FIG. 1) of the laryngoscope, e.g., via adjusting different geometrical parameters of the base plate and or top plate of the speculum and determining the degree of visual access for each set of geometrical parameters so as to arrive at optimal values of those parameters. For example, in some cases, computerized design software can be used for modeling and adjusting various geometrical parameters of the laryngoscope. In some embodiments, an expert medical professional may determine the degree of exposure provided by each set of the geometrical parameters until an optimized set is achieved. In other embodiments, a computerized system can define and optimize a figure-of-merit indicative of the degree of exposure of an anatomical tissue of interest for a given set of the geometrical parameters of the laryngoscope and arrive at an optimal set of parameters based on optimizing (e.g., maximizing) that figure-of-merit. By way of example, and without limitation, in some embodiments, the figure-of-merit can be defined as a maximum tilt of a surgical microscope that is optically coupled to the instrument relative to a longitudinal axis of the instrument that can be used for viewing a surgical site of interest in the aerodigestive tract of a patient or a group of patients. Other figures-of-merit can also be defined and employed in the practice of the present teachings.

In some embodiments, the optimized geometry output obtained for the laryngoscope can then be integrated into a computer-aided design program and used with an additive manufacturing method, such as three-dimensional printing, to create a tailored speculum/device that is highly customized to allow for optimal exposure of the desired anatomical region.

In some embodiments, the materials for fabricating the speculum of the laryngoscope can be selected (metals, plastics, composites) based on the shape, contour, size, ergonomics, anatomical stiffness (e.g., post radiation treatment) and other requirements so as to produce an optimal speculum (instrument), for example, for a custom-tailored instrument for a particular individual or a group of patients. For example, when a patient's anatomical tissue of interest is stiffer and less distensible than normal tissue, e.g., due to previous exposure to radiation, e.g., for treatment of cancerous lesions, rigid metal materials are used for the fabrication of the speculum, such as its base plate and/or top plate, due to the lack of distensibility of the soft tissues. Some examples of materials that can be used for the fabrication of the speculum include without limitation, titanium, stainless steel, cobalt-chrome, aluminum, and polymeric materials employed in 3-D printing applications.

A large number of laryngoscopes have been designed over the last 120 years to accommodate the variety of human anatomical characteristics, thereby producing many incremental design changes for Otolaryngologists (throat surgeons), anesthesiologists, oral surgeons and dentists. However, the majority of these designs have been dedicated to translaryngeal orotracheal intubation for the administration of general anesthesia. The viewing exposure required for this task is primarily limited to viewing the interarytenoid region of the glottal introitus for passage of an endotracheal tube into the trachea to administer general anesthesia. The design of laryngoscopes, pharyngoscopes, and oral cavity retractors typically present more challenges as significantly wider viewing field is required for performing surgery. Anatomical regions such as but not limited to the anterior glottal commissure of the larynx and the pyriform sinus of the laryngopharynx are mechanically more difficult to expose. Performing surgery on these anatomical regions is made even more difficult by the frequent use of a magnifying surgical microscope with binocular objectives and a front lens. The optics of the converging images of a surgical microscope require a wider proximal lumen for a laryngoscope or pharyngoscope further complicating the requirements of the proximal size and shape of an endoscopic speculum. When feasible, maintaining the use of the surgical microscope is advantageous since it provides the operator with stereoscopic viewing and depth perception along with delicate bimanual tactile proprioception of soft tissue during magnified tissue dissection. These precise microsurgical advantages are not available when employing surgical technologies that rely on flexible or curving endoscopes that provide a view that requires the surgeon to use one eye or a screen to use both eyes. Viewing technologies of the larynx that are associated with simpler manual tasks (e.g., orotracheal intubation) can be achieved without a surgical microscope. However, highly delicate bimanual surgery optimized by proprioception (e.g., larynx, eye, brain) are best suited for a surgical microscope. Unlike the eye or brain, the larynx and pharynx require complex endoscopic speculum to provide the exposure and instruments are fewer in number. Moreover, the design requirements for optimal exposure of a surgical operative site within the upper aerodigestive tract cavity (e.g., to remove a tumor), along with the forces required to displace soft tissue for that exposure, compound the economic manufacturing feasibility of optimal instrumentation that can achieve these mandates. Consequently, the methods of fabricating laryngoscopes as disclosed herein allow for groups of similar patients or even an individual patient to have a custom-tailored laryngoscope/pharyngoscope that can be employed for diagnostic and/or therapeutic procedures performed on that patient.

In another aspect of the present teachings, the methods disclosed herein can also be employed to analyze previously-fabricated laryngoscopes, or other transoral instruments (e.g., those fabricated based on conventional methods, e.g., via economically sound production (tooling) techniques) to identify those features that are optimal for use, e.g., with an individual subject (e.g., patient) or a group of individuals (or as a universal laryngoscope) and also identify those features that are not optimal (e.g., those features that negatively impact the laryngoscope's function). Such analysis and efficient redesign and production of modified versions of existing laryngoscopes and pharyngoscopes by applying extremely nuanced detailed modifications thereto provide instruments with enhanced functionality for the physician and surgeon. By way of example, such an improved laryngoscope can be fabricated via making physical changes to an existing laryngoscope. By way of example, the structural strength of certain components/segments of an existing laryngoscope/pharyngoscope and/or certain geometrical parameters of the laryngoscope/pharyngoscope (e.g., the size of lateral slots) may be sub-optimal. As another example, such geometrical parameters may limit the delivery of light guides and/or suction cannula into the instrument. However, fabricating a new laryngoscope (e.g., using 3-D printing techniques) based on the enhanced design parameters, can precisely remove/modify the negative characteristics of the previously-fabricated laryngoscope by conventional tooling methods while retaining their positive characteristics.

Consequently, in some embodiments, the spectrum of specula/instruments that exist can be modified for enhanced function and three-dimensionally printed.

Referring now to FIG. 1, a laryngoscope 100 is shown in accordance with an exemplary embodiment, which can be designed and fabricated using the present teachings. The laryngoscope 100 may be modular. That is, each component of the laryngoscope 100 may be individually produced (e.g., by a three-dimensional (3D) printer or by another additive manufacturing system).

The laryngoscope 100 includes a speculum 102 having a base plate 104 that is removably coupled to a top plate 103. Although in this embodiment the top plate 103 and the base plate 104 are removably coupled to one another, in other embodiments, they can form an integral unit. As will be discussed in further detail herein, the speculum 102 may be made of a tissue-compatible material (e.g., capable of withstanding an acidic environment of a tissue) including, but not limited to metals, plastics, and composite materials and may be produced by a 3D printer. In some embodiments, the laryngoscope and/or pharyngoscope may have components of different materials. For example, top plate (i.e., an upper portion) of the speculum may be made of a metal to withstand retraction forces but the base plate, and cannulas for suction and lighting may be made of plastics that are disposable since these parts are more difficult to clean and sterilize. The choice of the materials may also be based on information in an anatomical profile of the throat of an individual patient or a group of patients. For example, an anatomical profile may include information regarding whether the patient had previously undergone throat radiation treatment. Generally, after radiation treatment, a tissue may lose some of its elasticity. In some embodiments, in addition to consideration regarding the elasticity of an anatomical tissue of interest, the ease of fabrication as well as the fabrication cost may inform the choice of materials for use in the fabrication of a laryngoscope.

The top plate 103 and the base plate 104 of the speculum 102 extend from a proximal end 106 to a distal end 108 of the laryngoscope 100. The top plate 103 includes a speculum wall 110 and a handle attachment element 112. The handle attachment element is configured to attach to an "L" shaped handle (not shown) that allows a surgeon to hold and operate the laryngoscope 100, e.g., in a manner known in the art.

Figure 2:
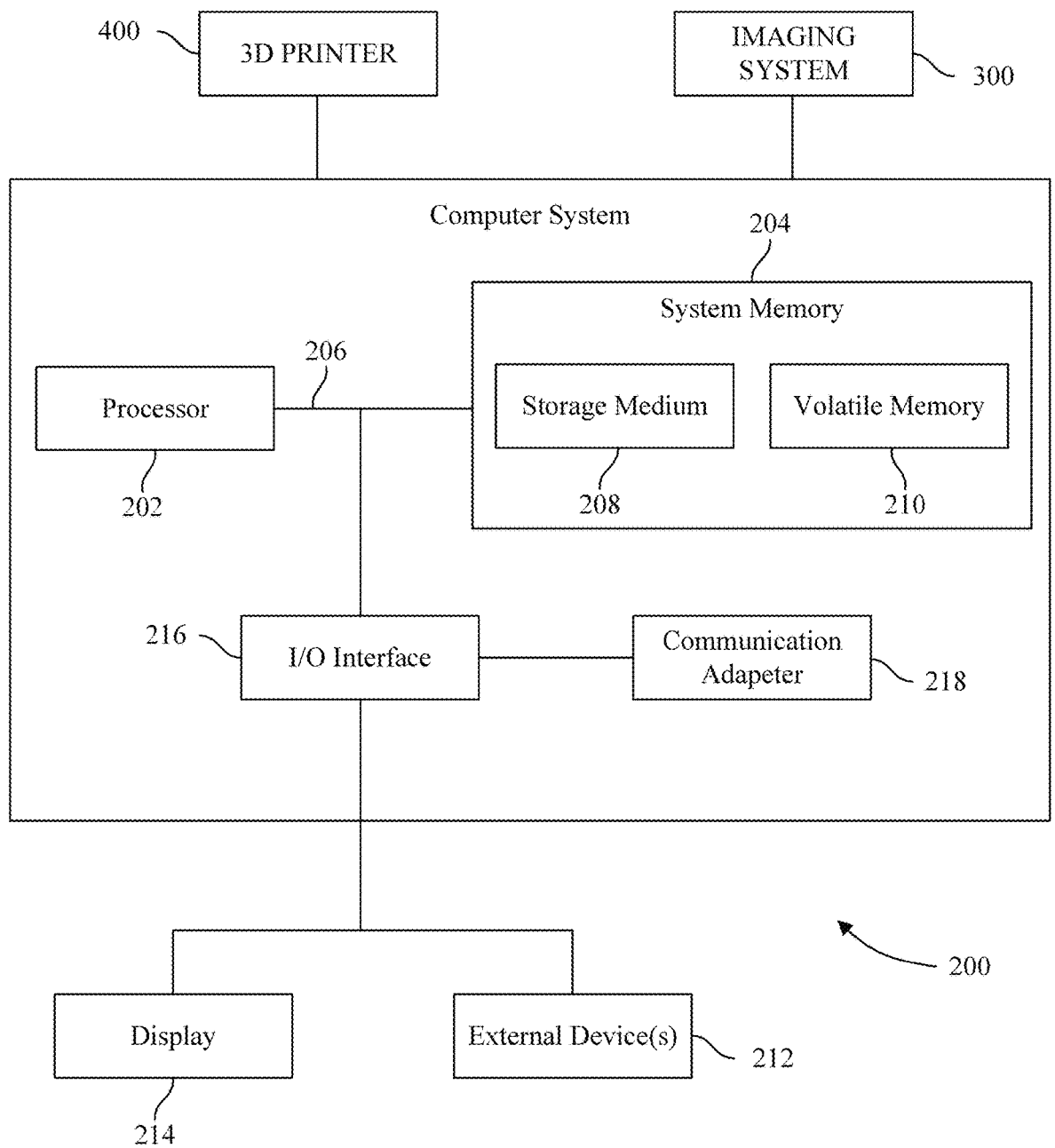
FIG. 2 diagrammatically depicts a computer system in accordance with an exemplary embodiment.

Referring now to FIG. 2, a computer system 200 is shown in accordance with an exemplary embodiment. As used herein a computer system (or device) is any system/device capable of receiving, processing, and/or sending data. Examples of computer systems include, but are not limited to personal computers, servers, hand-held computing devices, tablets, smart phones, multiprocessor-based systems, mainframe computer systems, and distributed cloud computing environments that include any of the above systems and the like.

As shown in FIG. 2, the computer system 200 includes one or more processors or processing units 202, a system memory 204, and a bus 206 that couples various components of the computer system 200 including the system memory 204 to the processor 202.

The system memory 204 includes a computer-readable storage medium 208 and volatile memory 210 (e.g., Random Access Memory, cache, etc.). As used herein, a computer-readable storage medium includes any media that is capable of storing computer readable program instructions and is accessible by a computer system. The computer-readable storage medium 208 includes non-volatile and non-transitory storage media (e.g., flash memory, read-only memory (ROM), hard disk drives, etc.). Computer readable program instructions as described herein include program modules (e.g., routines, programs, objects, components, logic, data structures, etc.) that are executable by a processor. Furthermore, computer readable program instructions, when executed by a processor, can direct a computer system (e.g., the computer system 200) to function in a particular manner such that a computer-readable storage medium (e.g., the computer-readable storage medium 208) comprises an article of manufacture. Specifically, the execution of the computer readable program instructions stored in the computer-readable storage medium 208 by the processor 202 creates means for implementing the functions specified in the method 400 depicted in FIG. 4 and the method 500 depicted in FIG. 5.

The bus 206 may be one or more of any 200 of bus structure capable of transmitting data between components of the computer system 200 (e.g., a memory bus, a memory controller, a peripheral bus, an accelerated graphics port, etc.).

In some embodiments, as depicted in FIG. 2, the computer system 200 may include one or more external devices 212 and a display 214. As used herein, an external device includes any device that allows a user to interact with a computer system (e.g., mouse, keyboard, touch screen, etc.). An external device 212 and the display 214 can be in communication with the processor 202 and the system memory 204 via an Input/Output (I/O) interface 216.

The display 214 may display a graphical user interface (GUI) that may include a plurality of selectable icons and/or editable fields. A user may use an external device 212 (e.g., a mouse) to select one or more icons and/or edit one or more editable fields. Selecting an icon and/or editing a field may cause the processor 202 to execute computer readable program instructions stored in the computer readable storage medium 208. In one example, a user may use an external device 212 to interact with the computer system 200 and cause the processor 202 to execute computer readable program instructions relating to the method 400 depicted in FIG. 4 and the method 500 depicted in FIG. 5.

The computer system 200 may further include a network adapter 218 which allows the computer system 200 to communicate with one or more other computer systems/devices via one or more networks (e.g., a local area network (LAN), a wide area network (WAN), a public network (the Internet), etc.).

The computer system 200 may be in wired or wireless communication with a medical imaging system 300. The computer system 200 may be in wireless communication with the medical imaging system 300 when the computer system 200 and the medical imaging system 300 are connected to a same network. The medical imaging system 300 is configured to generate image data of the throat and/or tissues that surround the throat.

In one embodiment, the medical imaging system 300 is an imaging system capable of imaging, e.g., using any suitable imaging modality such as X-ray, ultrasound, and/or magnetic resonance imaging, an internal anatomy of throat (e.g., a flexible endoscope, a rigid endoscope, etc.) thereby producing image data. In some embodiments, the display 214 or a display of the medical imaging system 300 displays the image data.

In another embodiment, the medical imaging system 300 is a computed tomography (CT) imaging system. In such an embodiment, the medical imaging system 300 includes radiation source and a radiation detector. The radiation source emits radiation that traverses an examination region that includes a patient's head and/or throat. The radiation is attenuated by biological material (e.g., bone, tissue, etc.) within the examination region. The radiation detector detects the attenuated radiation and generates a plurality of signals indicative of the detected radiation. A reconstructor of the medical imaging system 300 processes the signals and generates image data based on the processed signals. In some embodiments, the display 214 or a display of the medical imaging system 300 displays the image data.

In yet another embodiment, the medical imaging system 300 is a magnetic resonance imaging (MRI) system. In such an embodiment, the medical imaging system includes a plurality of magnets, a radiofrequency emitter, and an electromagnetic energy detector. The magnets produce a magnetic field that traverses an examination region that includes the patient's head and/or throat. The magnetic field forces protons within biological material within the examination region to align with respect to the magnetic field. Then, the radiofrequency emitter emits a radio frequency that forces the protons to change their alignment with respect to the magnetic field. When the radiofrequency emitter is turned off, the protons realign with respect to the magnetic field and release electromagnetic energy. The electromagnetic energy detector detects the released electromagnetic energy and generates signals indicative of the detected electromagnetic energy. A reconstructor of the medical imaging system processes the signals and generates image data based on the processed signals. In some embodiments, the display 214 or a display of the medical imaging system 300 displays the image data.

As will be discussed in further detail herein, the image data may be further analyzed by a processor (e.g., the processor 202) to determine one or more anatomical parameters of the patient's throat (e.g., such as the jaw-opening capacity, size and/or shape of the mouth and throat). In another embodiment, the image data may be further analyzed by a processor (e.g., the processor 202) to determine rheometric data of the patient (e.g., tissue distensibility (rheometry) diminishment from radiation or trauma).

In one embodiment, the imaging system captures rheometric data. In another embodiment, a rheometer captures rheometric data.

The computer system 200 may be in wired or wireless communication with a three-dimensional (3D) printer 400. The computer system 200 may be in wireless communication with the 3D printer 400 when the computer system 200 and the 3D printer 400 are connected to a same network. The 3D printer 400 is configured to generate components of the laryngoscope 100 based on an anatomical profile of a patient or a group of patients. For example, the 3D printer 400 is configured to generate the top plate 102 and/or the base plate 104.

Figure 3:
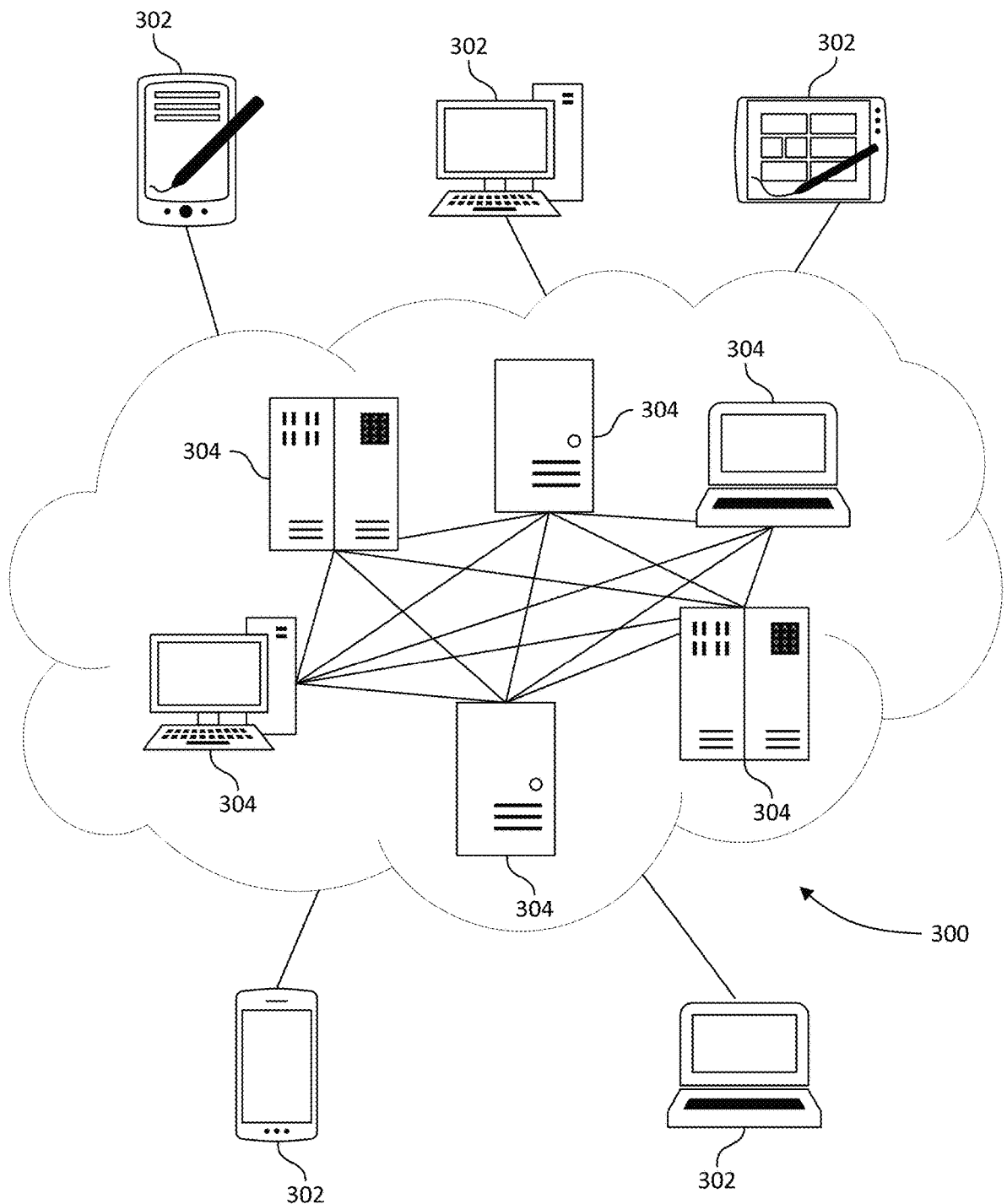
FIG. 3 diagrammatically depicts a cloud computing environment in accordance with an exemplary embodiment.

Referring now to FIG. 3 a cloud computing environment 300 connected to one or more user computer systems 302 is depicted in accordance with an exemplary embodiment. The cloud computing environment 300 provides network access to shared computing resources (e.g., storage, memory, applications, virtual machines, etc.) to the one or more user computer systems 302 As depicted in FIG. 3, the cloud computing environment 300 includes one or more interconnected nodes 304. Each node may be a computer system or device with local processing and storage capabilities. The nodes 304 may be grouped and in communication with one another via one or more networks. This allows the cloud computing environment 300 to offer software services to the one or more user computer systems 302 and as such, a user computer system 200 does not need to maintain resources locally.

Figure 4:
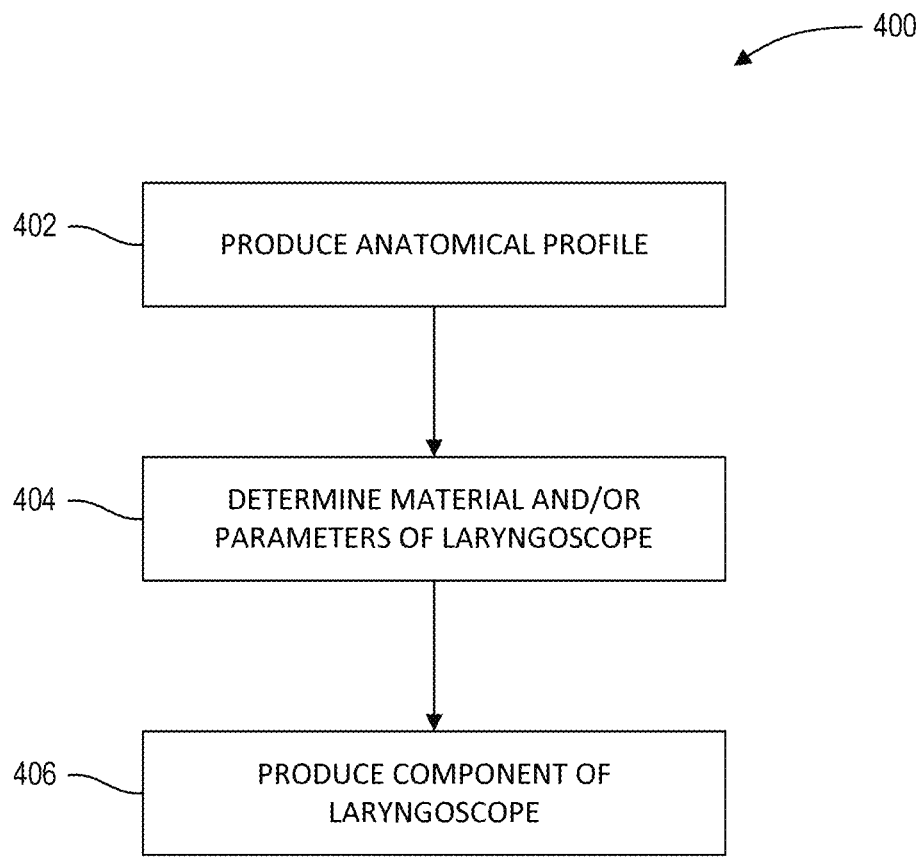
FIG. 4 is a flow chart of a method for producing a laryngoscope in accordance with an exemplary embodiment.
Figure 5:
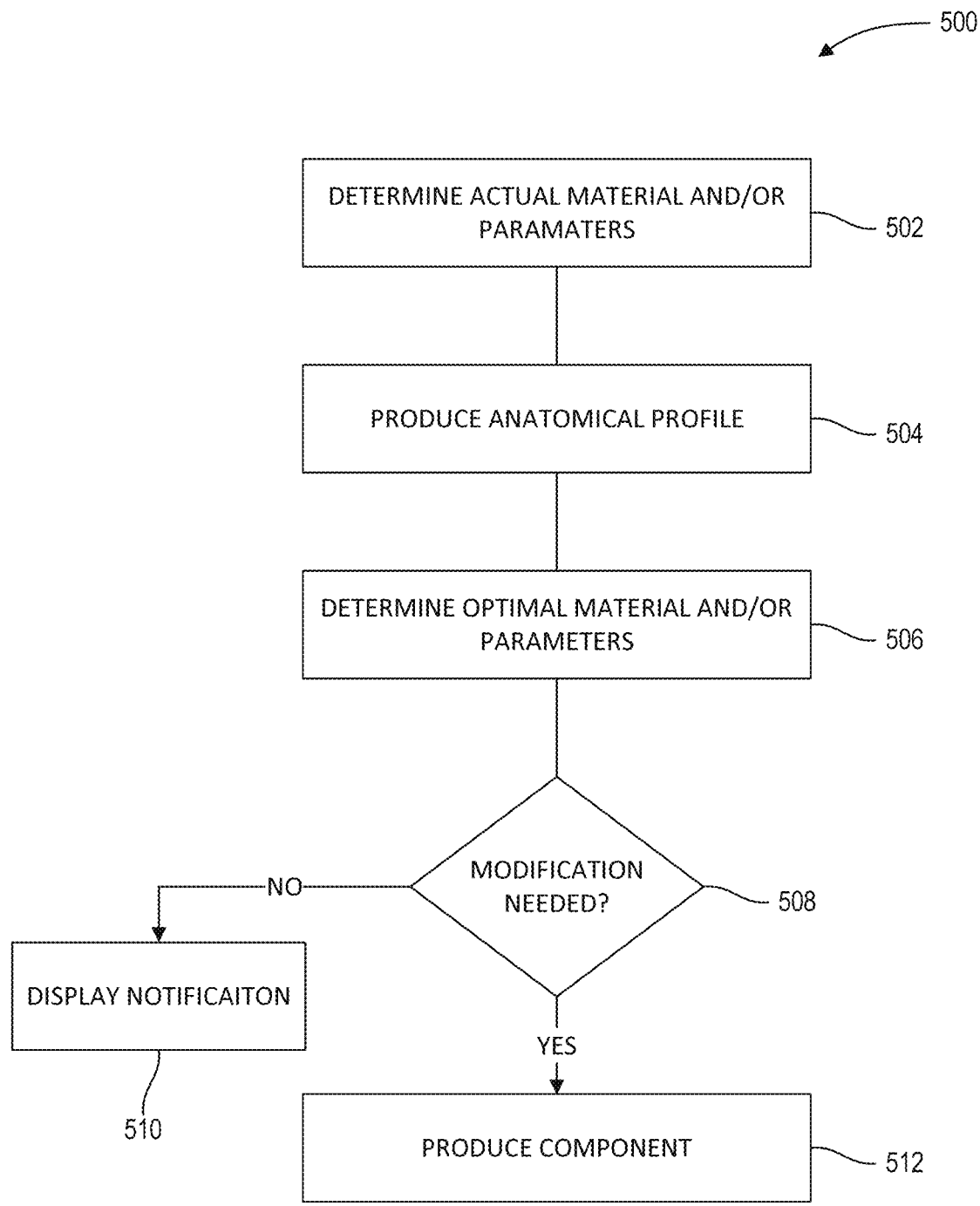
FIG. 5 is a flow chart of a method for analyzing geometric parameters of a laryngoscope in accordance with an exemplary embodiment.

In one embodiment, a node 304 includes the system memory 204 and as such, includes the computer readable program instructions for carrying the method 400 of FIG. 4 and the method 500 depicted in FIG. 5. In such an embodiment, a user of a user computer system 200 that is connected to the cloud computing environment 300 may cause a node 304 to execute the computer readable program instructions to carry out the method 400 or the method 500.

Referring now to FIG. 4, a method 400 for producing a laryngoscope is shown in accordance with an exemplary embodiment. As previously discussed herein, the steps 402-406 of the method 400 may be stored as computer readable program instructions in a computer readable storage medium (e.g., the computer readable storage medium 208). A processor that is configured according to an aspect of the present disclosure (hereinafter "a configured processor") executes the computer readable program instructions for the method 400. In one embodiment, the configured processor is the processor 202.

At 402, the configured processor produces an anatomical profile for a patient or a group of patients. The anatomical profile contains patient information and/or information relating to the neck, head, and/or the jaw of the patient (e.g., anatomical parameters, age, gender, prior medical history, etc.). The anatomical profile may be based on image data generated by the medical imaging system 300. For example, the medical imaging system may produce image data of a larynx. Based on the image data, the configured processor may determine the length of the oropharynx and add the length of the oropharynx to the anatomical profile. In another example, the configured processor may determine, based on an electronic medical record of the patient, the patient previously underwent throat surgery. In this example, the configured processor adds this information to the anatomical profile. The anatomical profile may further be based on rheometric measurements of the head, neck, and jaw. For example, the configured processor may integrate solid restrictions such as cephalometric bony anatomy, with the size and position of the soft tissues and integrate with the distensibility of the soft tissue based on rheometric data in an individual patient's soft tissue (e.g., tongue, palate, pharyngeal musculature, laryngeal musculature) or the soft tissue associated with a group of patients. In another example, the configured processor determines a 3D shape, contour, size, caliber, and relational difference of the airway based on image data (captured by the imaging system) and/or rheometric data.

At 404, the configured processor determines material and/or geometrical parameters of a laryngoscope based on the anatomical profile. The configured processor may determine the parameters in a computerized model of the laryngoscope. The configured processor chooses optimal material and/or optimal geometric parameters that will produce a laryngoscope that will allow for optimal exposure of a desired anatomical region as the determined material and/or geometric parameters and/or minimize the risk of damage to the patient's throat tissue when employed.

At 406, the configured processor sends a signal to produce a component of a laryngoscope based on the determined material and/or geometric parameters to a laryngoscope component-producing element (e.g., a 3D printer). In response to receiving the signal to produce a component of a laryngoscope, the laryngoscope component producing element produces the component based on the determined material and/or geometric parameters.

Referring now to FIG. 5, a method 500 for analyzing geometric parameters of a laryngoscope is shown in accordance with an exemplary embodiment. As previously discussed herein, the steps 502-512 of the method 500 may be stored as computer readable program instructions in a computer readable storage medium (e.g., the computer readable storage medium 208). A configured processor executes the computer readable program instructions for the method 500. In one embodiment, the configured processor is the processor 202.

At 502, the configured processor determines an actual geometric parameter and/or actual material of a laryngoscope with or without intervention from a user of a computer system with the configured processor. The configured processor determines the geometric parameter(s) of the laryngoscope by analyzing the laryngoscope. In another embodiment, a user of a computer system with the configured processor may manually input am actual geometric parameter and/or material and the configured processor determines the actual geometric parameter based on the user input.

At 504, the configured processor produces an anatomical profile of a patient or a group of patients (e.g., characterized as an average of anatomical parameters associated with a sample of patients in that group) as previously discussed herein with respect to 402.

At 506, the configured processor determines an optimal material and/or geometric parameters of a laryngoscope based on the anatomical profile as previously discussed herein with respect to 504.

At 508, the configured processor determines if a component of the laryngoscope needs modification by comparing the determined optimal materials and/or geometric parameters to the determined actual geometric parameter(s) and/or determined actual material of the laryngoscope. The configured processor determines a component needs modification when a determined optimal material and/or geometric parameter and a determined actual material and/or geometric parameter are different.

At 510, in response to determining no components need modification, the configured processor causes a display (e.g., the display 214) to display a notification indicating no components need modification.

At 512, in response to determining that a component needs modification, the configured processor sends a signal to produce the component based on the determined optimal material and/or geometric parameters to a laryngoscope component producing element. For example, the design information can be uploaded in an appropriate format onto a 3-D printing device for fabricating the laryngoscope.

As noted above, in some embodiments, one or more geometrical parameters of a laryngoscope according to the present teachings can be adjusted based on the derived anatomical profile of a subject or a group of subjects to obtain an optimal visual access to an anatomical tissue of interest. By way of example and without limitation, some examples of such geometrical parameters include the length of any of the top plate and/or the base plate of the speculum, the inner diameter of the lumen of the speculum, the radius of curvature of the speculum, a tilt angle of a proximal portion of the base plate relative to the rest of the base plate, among others. While the above methods 400 and 500 describe a method for producing or analyzing components of a laryngoscope, the above methods may be implemented to analyze and/or produce components of pharyngoscopes and oral cavity retractors.

As previously discussed, the above may be implemented by way of computer readable instructions, encoded or embedded on computer readable storage medium (which excludes transitory medium), which, when executed by a processor(s), cause the processor(s) to carry out the methods of the present disclosure.

While the invention has been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

The following Examples are provided to further elucidate various aspects of the present teachings and is not provided to indicate necessarily optimal ways of practicing the invention or optimal results that may be obtained.

EXAMPLES

Example 1

Figure 6A:
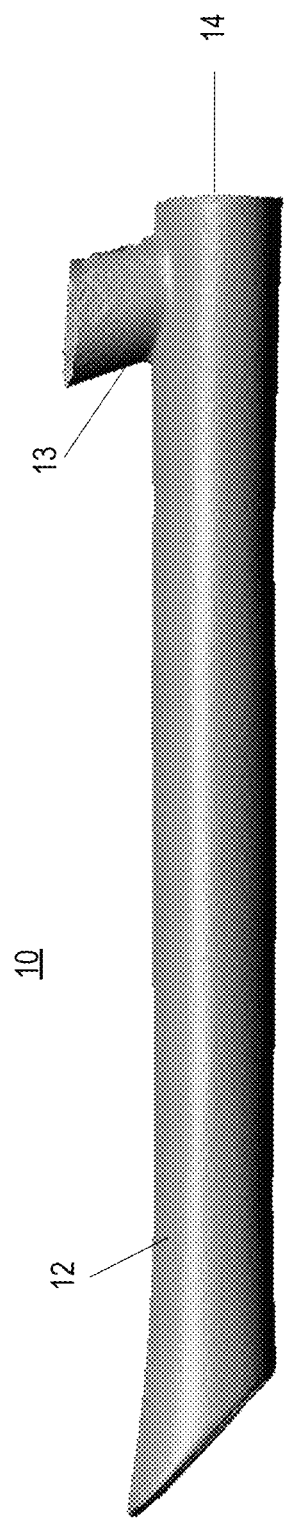
FIG. 6A schematically depicts a speculum of a conventional laryngoscope.
Figure 6C:
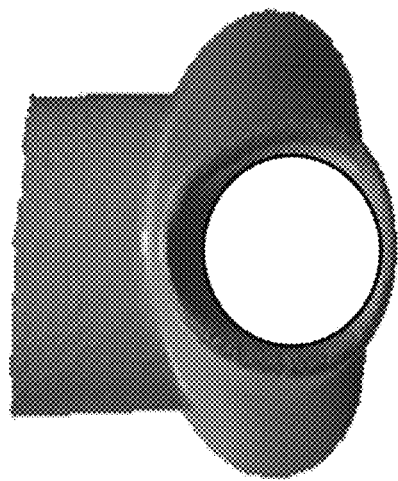
FIGS. 6B and 6C are schematic proximal and distal views of the speculum depicted in FIG. 6A, respectively.
Figure 6B:
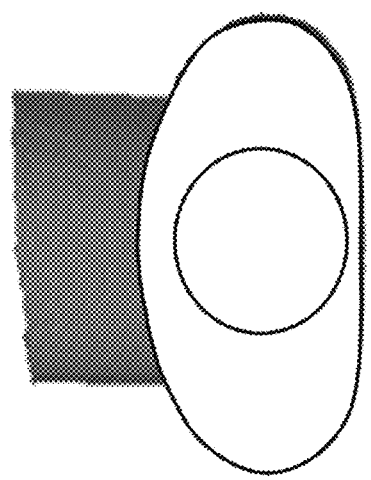

FIGS. 6A, 6B and 6C schematically depicts a conventional standard laryngoscope 10 this is used primarily for vocal cord microsurgery. Some surgeons prefer this laryngoscope because of the flare at the distal end of the speculum. The laryngoscope 10 includes a speculum 12 that extends from a proximal end (PE) to a distal end (DE). The laryngoscope 10 includes a handle attachment element 13 that allows coupling the speculum to a vertical handle for manipulating the speculum, e.g., for positioning the speculum in a patient's aerodigestive tract. The speculum 12 provides a lumen 14 for providing visual access to a surgical site. The speculum 12, however, suffers from a number of shortcomings. For example, the introduction of light into the lumen 14 would require clipping a light source in the lumen or introducing the light laterally into the lumen. These options can, however, result in at least partial obstruction of the lumen and/or inefficient illumination of the target site. Further, increasing the inner diameter of the lumen can result in a laryngoscope that is difficult to position within a patient's aerodigestive tract.

Figure 7A:
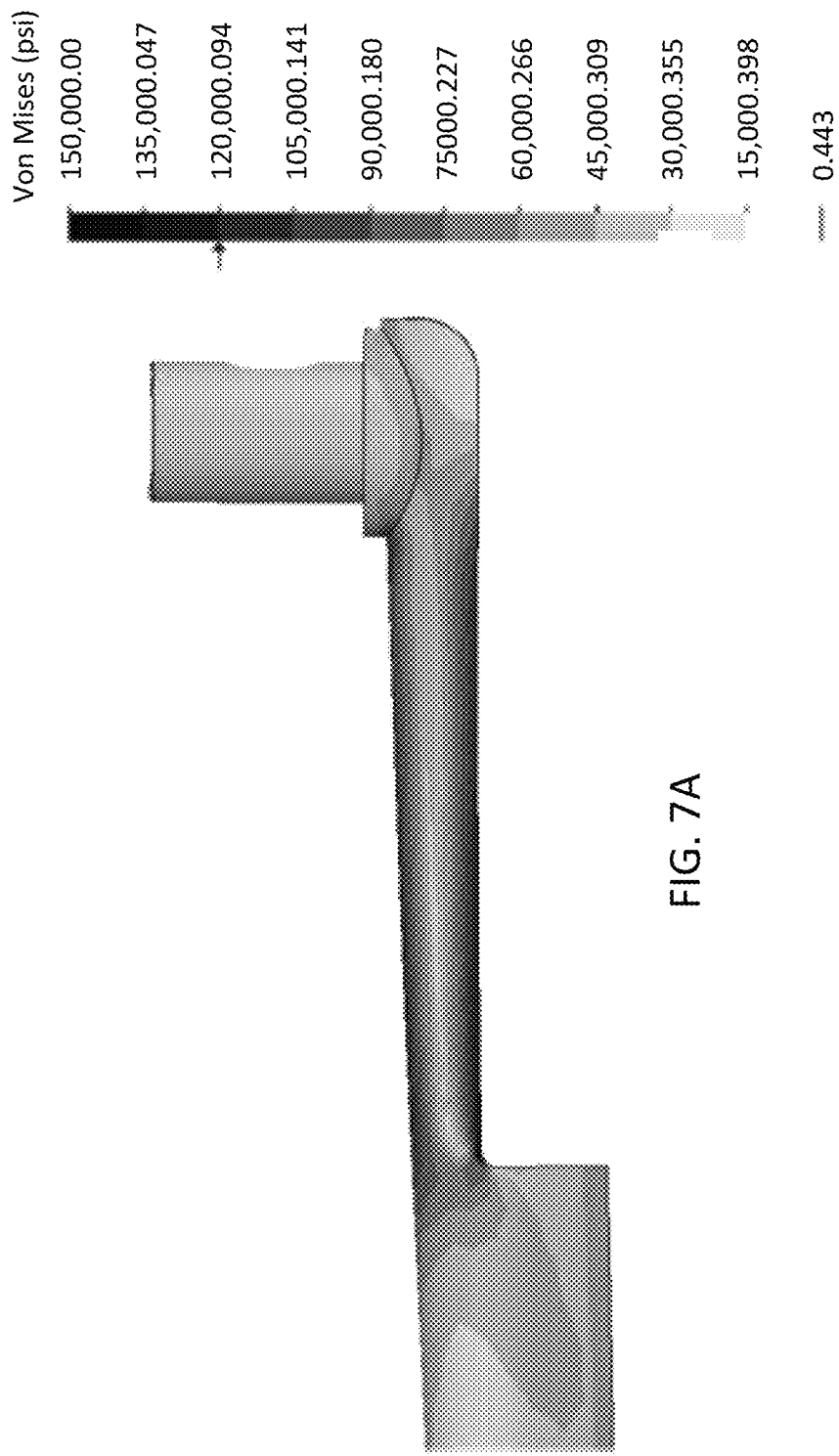
FIGS. 7A and 7B provide examples of calculated pressures, computed using finite element analysis, that are expected to be applied to the conventional speculum of FIG. 6A when used by a surgeon to provide access to a surgical site in the aerodigestive tract.
Figure 7B:
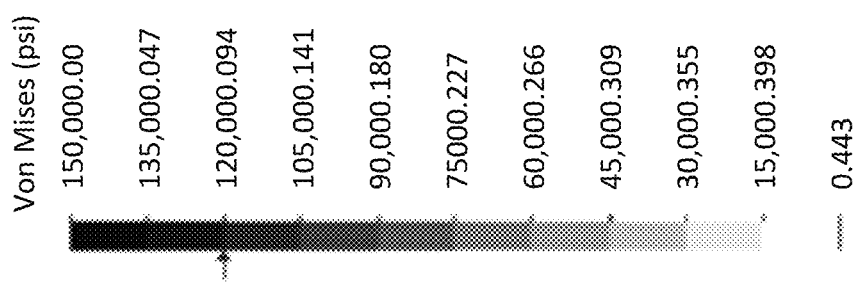
Figure 7B:
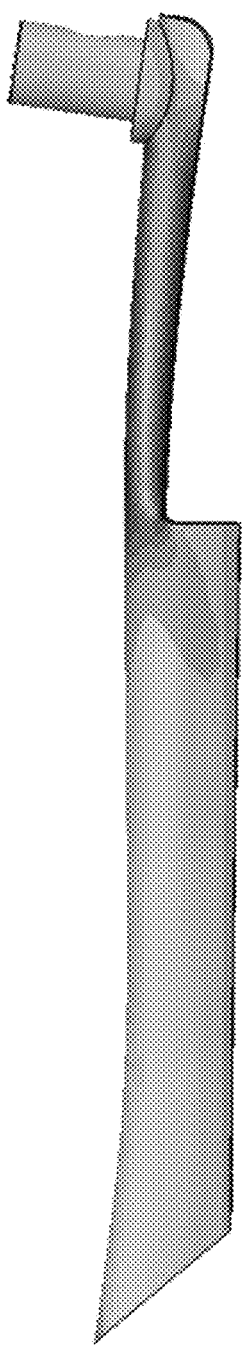

FIGS. 7A and 7B present structural finite element analysis of forces/pressures to which such a laryngoscope can be subjected in use, demonstrating instability and deformation that can occur with forces associated with a suspension gallows.

Example 2

Figure 8A:
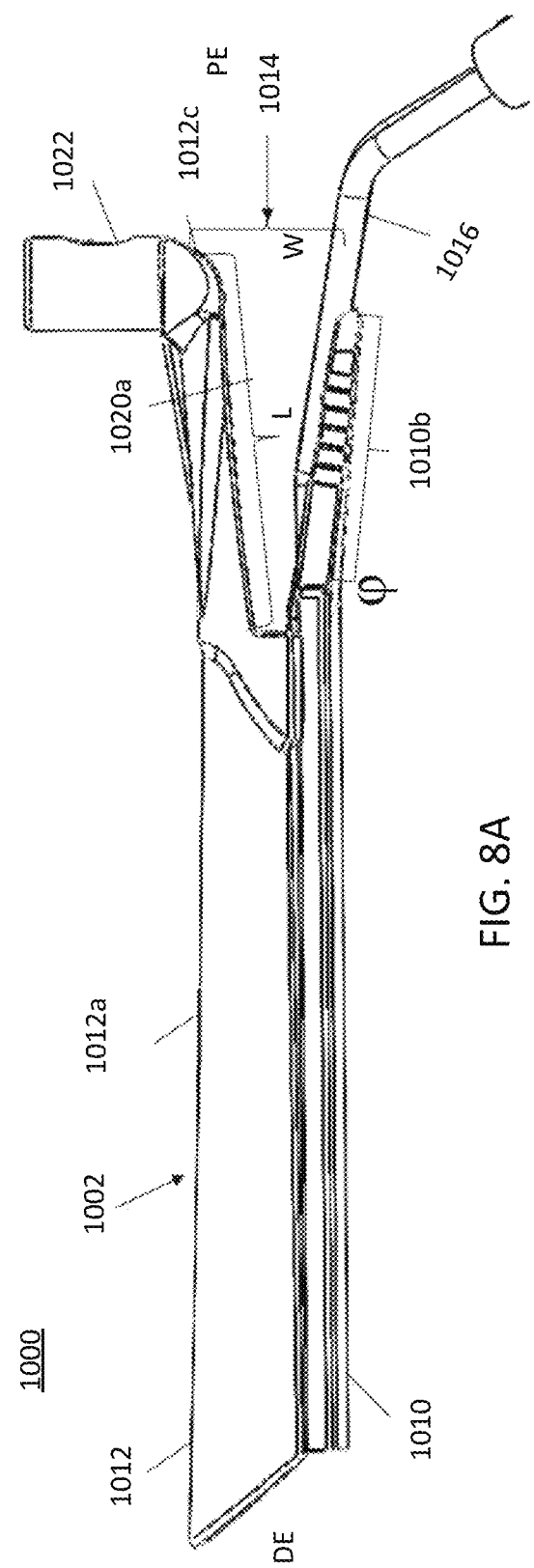
FIG. 8A is a schematic view of a speculum of a laryngoscope according to an embodiment of the present teachings.
Figure 8E:
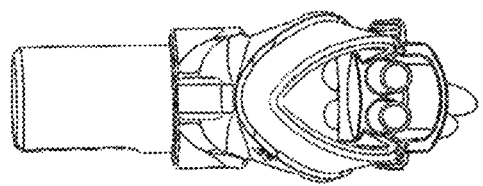
FIGS. 8B, 8C, 8D, and 8E are, respectively, the proximal view, the distal view angled up, the distal view angled down, and the distal view angled down (with additional tilt relative to FIG. 8D), of the speculum of FIG. 8A.
Figure 8D:
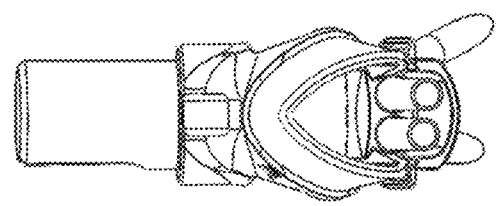
Figure 8C:
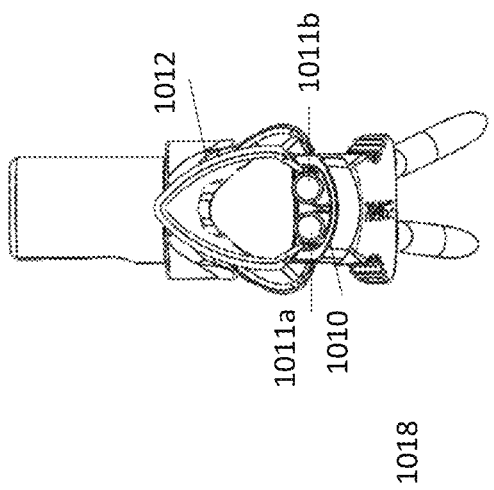
Figure 8B:
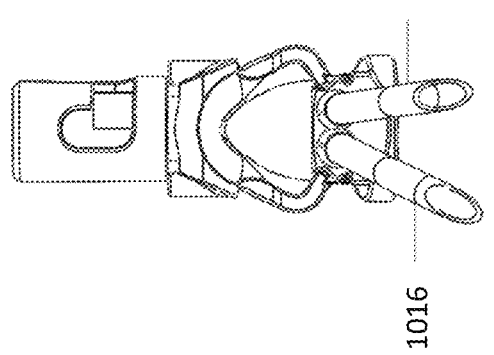

FIGS. 8A, 8B, 8C, 8D, and 8E show a slim Universal Glottiscope speculum 1000 according to an embodiment of the present teachings (the handle to which the speculum can be attached is not shown). More specifically, FIG. 8A is a side view of the speculum depicting a top plate 1012 that is coupled to a base plate 1010. FIG. 8B (proximal view) shows a cutaway view of removable light and suction cannulas 1016/1018 that are positioned in channels in the base plate. FIG. 8C (distal view angled up) shows widened distal end of the speculum from the centralized aspect where the speculum narrows to accommodate the glossotonsillar sulcus and posterior floor-of-mouth. FIG. 8D (distal view angled down) shows the inside of the distal speculum where the suction and light cannulas are situated along the inner floor of the base plate. FIG. 8E (distal view angled down more) shows the removable suction and light cannulas retracted to better demonstrate the inside depth of the distal base plate. The angled distal views can be fully utilized by titling a surgical microscope used to view a surgical site using the speculum.

The speculum 1000 can be fabricated using, a suitable metal, e.g., a cobolt-chromium alloy and employing 3-D printing fabrication techniques.

The speculum 1000 extends from a proximal end (PE) to a distal end (DE). The base plate 1010 (herein also referred to as the bottom plate or the bottom portion) that can be removably engaged with the top plate 1012 of the speculum so as to provide a lumen 1014 through which visual access to a target site, e.g., a patient's larynx, can be achieved. As noted above, the two cannulas 1016/1018 can be coupled to the speculum, where one of the cannulas is used for providing suction and the other is used for introducing an optical fiber into the speculum for illuminating the target site.

Various features of the base plate and the top plate of the speculum have been designed to maximize visual access to a target site while ensuring that the speculum can withstand forces applied thereto during use.

Figure 9B:
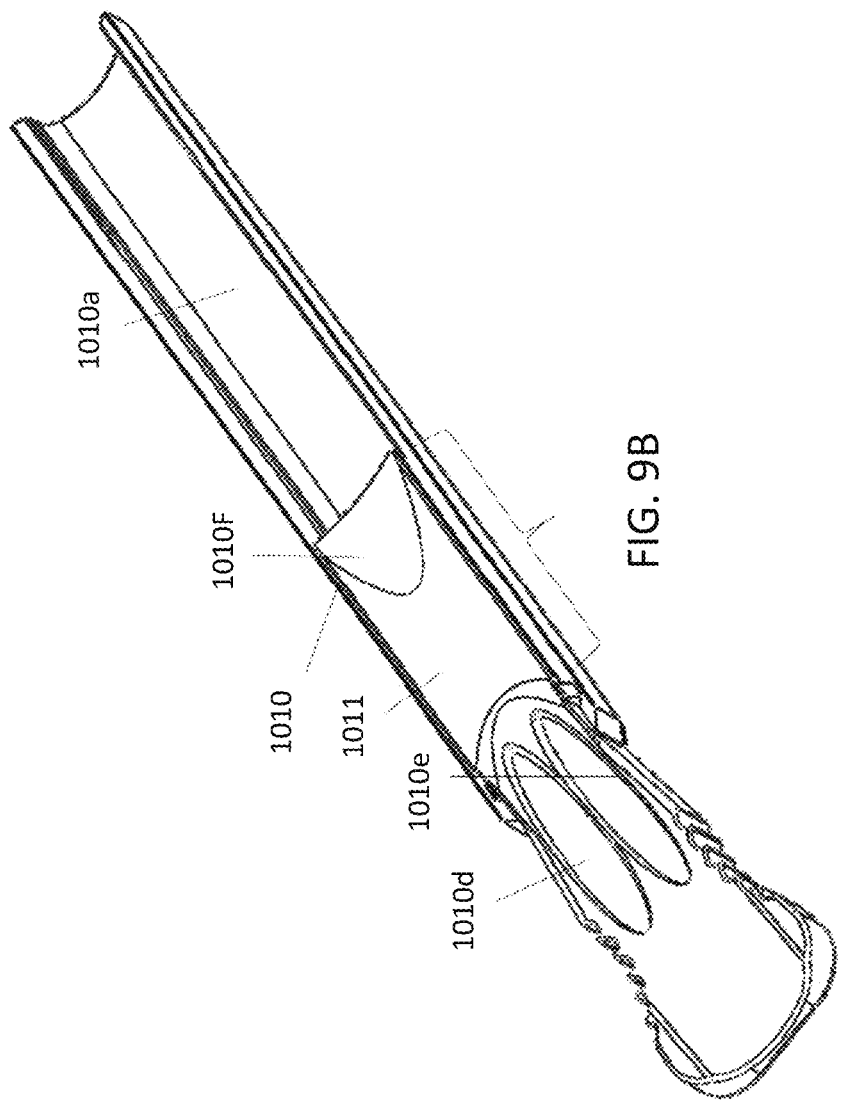
FIGS. 9A and 9B are top views of the base plate of the speculum depicted in FIG. 8A, depicting a curved bottom surface of the base plate.
Figure 9A:
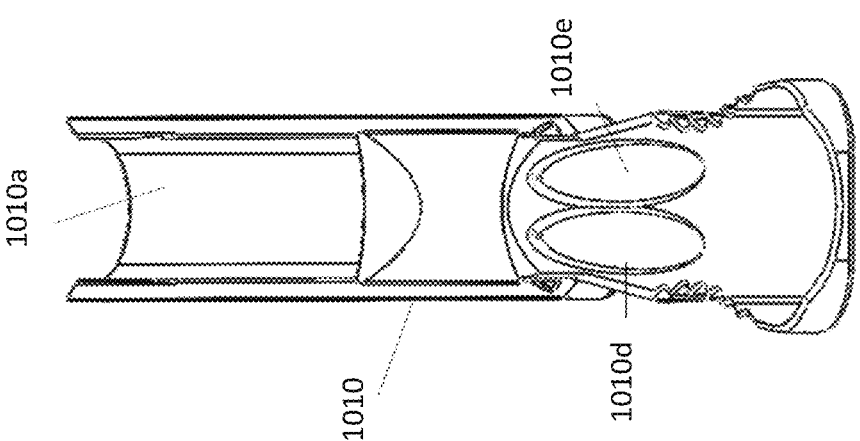

For example, with reference to FIGS. 9A and 9B, the base plate 1010 slides into the top plate (herein also referred to as the upper aspect) of the speculum and includes a curved bottom surface 1010a (also referred to as the bottom wall), rather than a flat bottom surface to increase the inner diameter of the lumen 1014, thereby providing enhanced visual access to the target site. In some embodiments, the curved bottom surface of the base plate can be characterized by a plurality of radii of curvature. In some embodiments, the curved bottom surface of the base plate can be U-shaped, e.g., with short lateral vertical limbs and an arch that extends between the vertical limbs.

The base plate 1010 includes a proximal portion 1010b that is titled relative to the rest of the base plate, where the tilt is depicted by an angle 9. The tilt of the proximal portion of the base plate relative to the rest of the base plate can facilitate the introduction of two cannulas 1016/1018 without the obstruction of the laryngoscope's lumen.

With continued reference to FIGS. 9A and 9B, in this embodiment the proximal portion of the base plate 1010 includes two depressions 1010d/1010e (herein also referred to as cut-out portions), which have been formed by removing material forming the base plate. The depressions 1010d/1010e can increase the exposure of a surgical field in the posterior glottis and interarytenoid region.

With particular reference to FIG. 8A as well as 9A and 9B, a cover 1011 coupled to the base plate includes two channels 1011a/1011b through which the cannulas 1016/1018 can extend. The cover 1011 helps retain the cannulas within the speculum. In this example, the length (L) of the cover has been selected to be as small as possible to minimize any obstruction that the cover may present with respect to a surgeon's visual access to the target site while ensuring that cannulas are retained within the speculum. In this embodiment, the cover 1011 includes a cut-out 1011f that further enhances the visual access to the target site.

Further, the cannulas are removably positioned within the lumen of the speculum and hence can be removed, if desired, e.g., prior to commencement of a surgical procedure, to enhance the field of view provided by the speculum to the surgeon.

With particular reference to FIGS. 8A, the top plate 1012 of the speculum includes a curved top wall 1012a, where the top wall extends to two opposed side ledge portions 1012b that allow removable engagement of the top plate of the speculum with the base plate. The proximal end of the top plate 1012 includes a notch 1012c that further enhances the field of view that the speculum can provide to a surgeon.

With particular reference to FIGS. 8A, upon coupling of the base plate with the top plate to form the speculum, two opposed lateral slots (one of which 1022a is visible in the figure) are formed at a proximal portion of the speculum, which can facilitate viewing of the target site. In this embodiment, each lateral slot has a length (L), which can be defined as the distance between the most proximal end of the top plate and the entrance of the lumen 1014 (i.e., the proximal end of the lumen) and a maximum width (W), which is herein also referred to as the maximum height, i.e., the maximum vertical separation between the top plate and the bottom plate. The length and the width of the lateral slots are maximized while ensuring that the speculum retains sufficient structural integrity, e.g., via enforcement of certain portions thereof, to maximize the field-of-view presented to the surgeon and ensure that the speculum can withstand forces applied thereto during use. In general, the length and the height of the slots can be selected, e.g., based on an intended patient population and can vary, for example, based on age and gender. By way of example, and without limitation, in some embodiments the length of the slots can be in a range of about 5 mm to about 7 cm, e.g., 1 cm to about 5 cm, and the maximum height of the slots can be in a range of about 3 mm to about 2 cm, e.g., about 5 mm to about 1 cm.

Figure 9C:
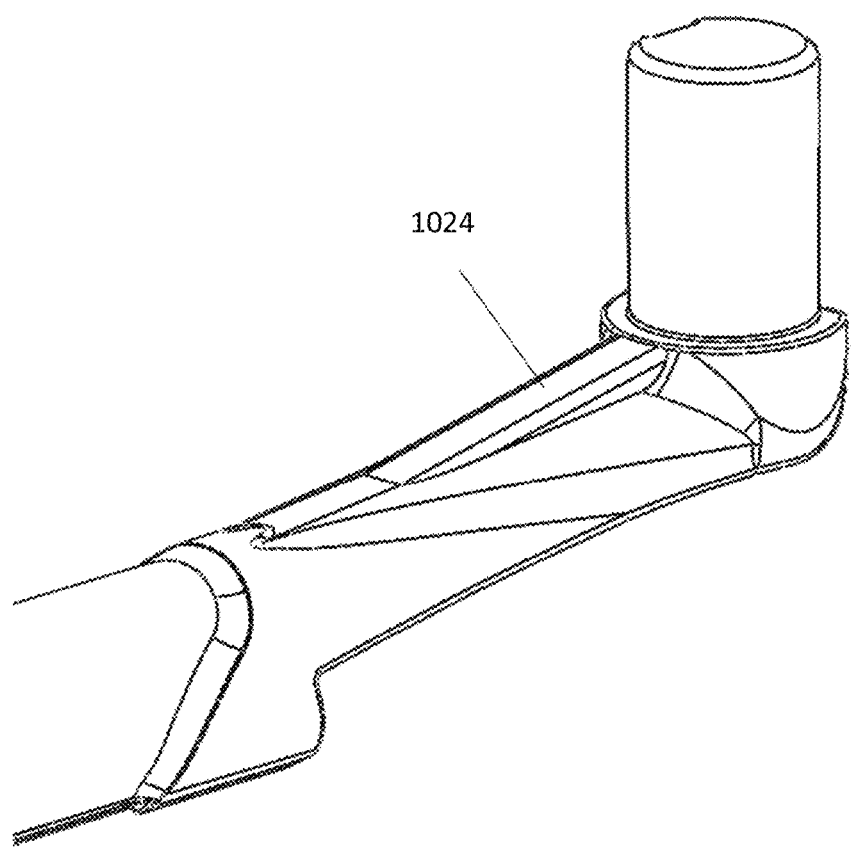
FIG. 9C is a schematic view of the proximal portion of the speculum depicted in FIG. 8A.
Figure 9D:
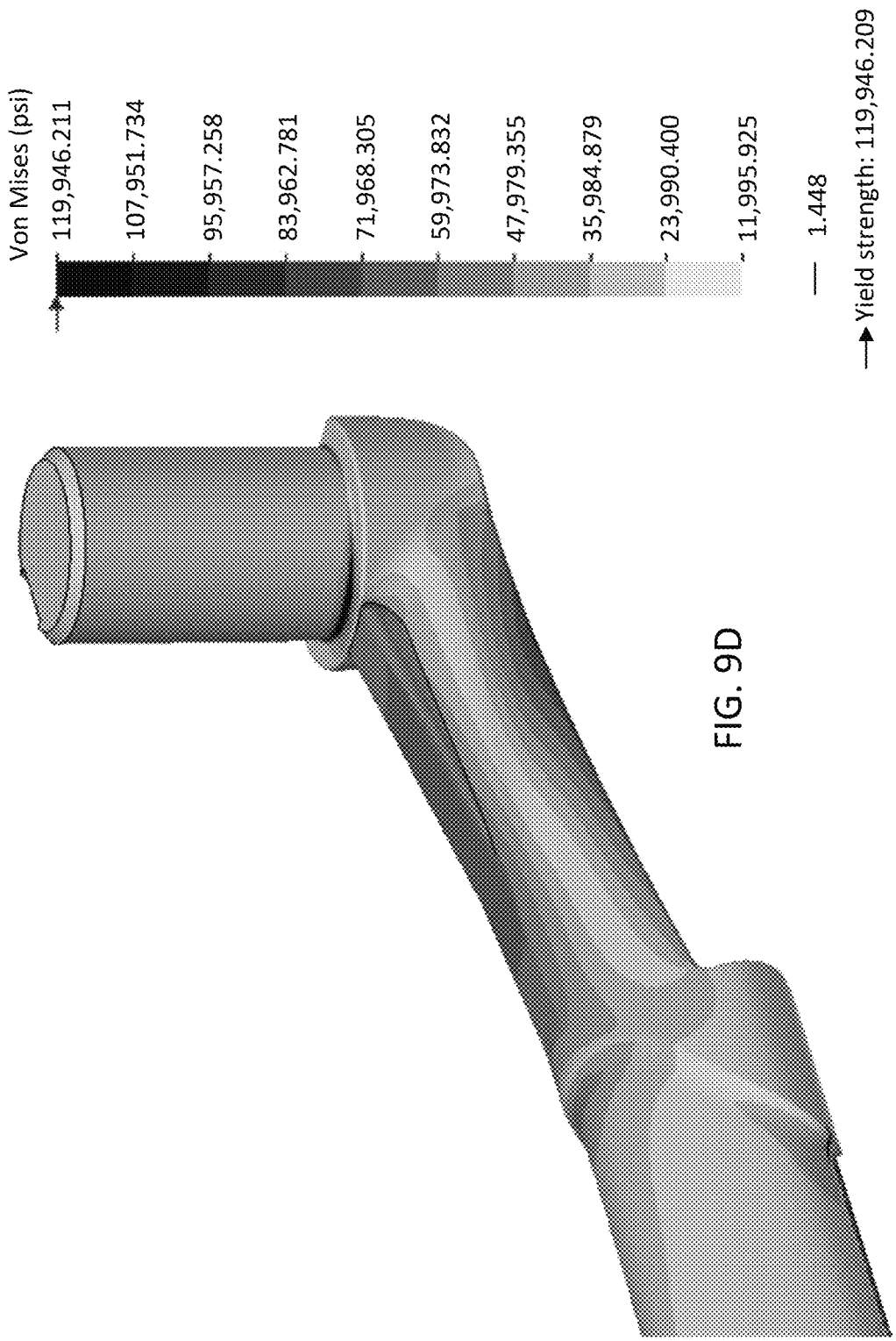
FIG. 9D shows the results of finite element analysis of pressures experienced by the proximal portion of the speculum depicted in FIG. 9C.

By way of example, structural finite element analysis can be employed to assess strain/stress pressures at various regions of the speculum, and in particular in a region in proximity of the junction between a handle attachment element 1022 and the top plate of the speculum. FIG. 9D shows theoretically-calculated maps of pressures experienced by various portions of the proximal aspect of the speculum during its use by a surgeon. Such structural finite element analysis of the stress/strain pressures to which various segments of the speculum are subjected during use can inform the reinforcement of those sections, e.g., by increasing the thickness of those sections and/or using a different material, e.g., a different metal, for forming those segments.

By way of example, it was discovered that increasing the length of the lateral slots may cause structural weakening of the connection between the handle attachment element and the top plate of the speculum. With particular reference to FIG. 9C, in order to address such potential structural weakening, additional material 1024 can be added to the top plate 1012 of the speculum in a region in proximity of the junction between the handle attachment element and the top plate to structurally reinforce this region by increasing its thickness, thereby providing additional structural support for withstanding forces applied during use of the speculum. More specifically, in this embodiment, the speculum include thicker metal and contoured midline rib that is designed to withstand the extreme forces on the top plate adjacent to the proximal slots and the connector (herein referred to also as the handle attachment element) for coupling the speculum to a vertical handle (not shown). For example, the thickness of the material 1024 can vary from about X mm to about X mm.

With reference to FIGS. 10A, 10B, 10C, and 10D, in some embodiments, the advantageous features of a transoral instrument according to the present teachings can be integrated with standard features of conventional instruments to achieve an enhanced instrument, e.g., via redesign of a standard instrument in accordance with the present teachings. For example, a speculum 2000 combines the proximal slots 2002/2004 and a base plate 2006 as disclosed herein, such as those discussed above in connection with the speculum 1000, with the distal portion of the top plate of a standard conventional speculum to form a hybrid speculum. It is noted that a notch 2006 formed at the proximal end of the speculum's top plate further enhances the visual access to a surgical site.

Figure 10A:
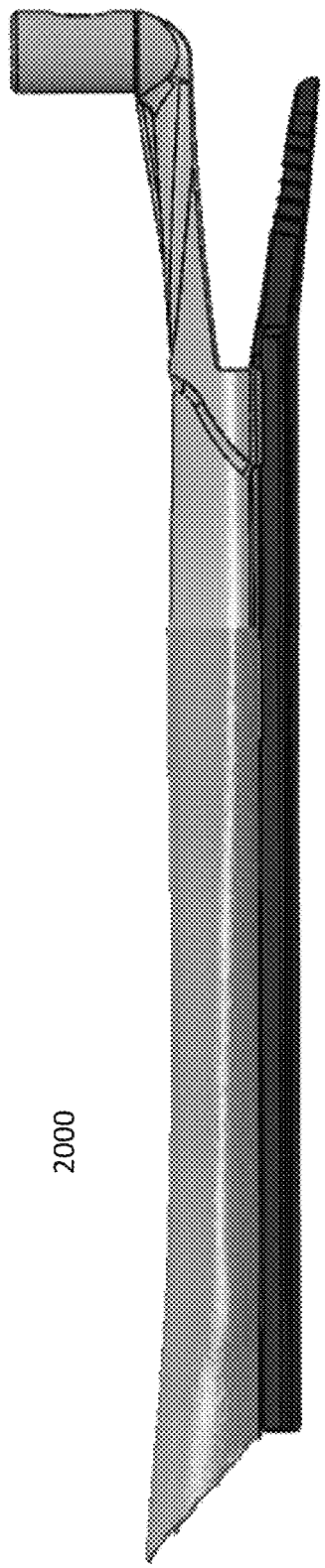
FIG. 10A is a side schematic view of a speculum that incorporates features of a conventional speculum as well as several features disclosed herein.
Figure 10C:
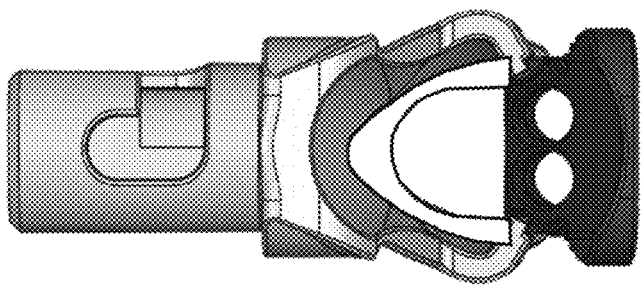
FIG. 10C is a proximal axial view of the speculum depicted in FIG. 10A.
Figure 10B:
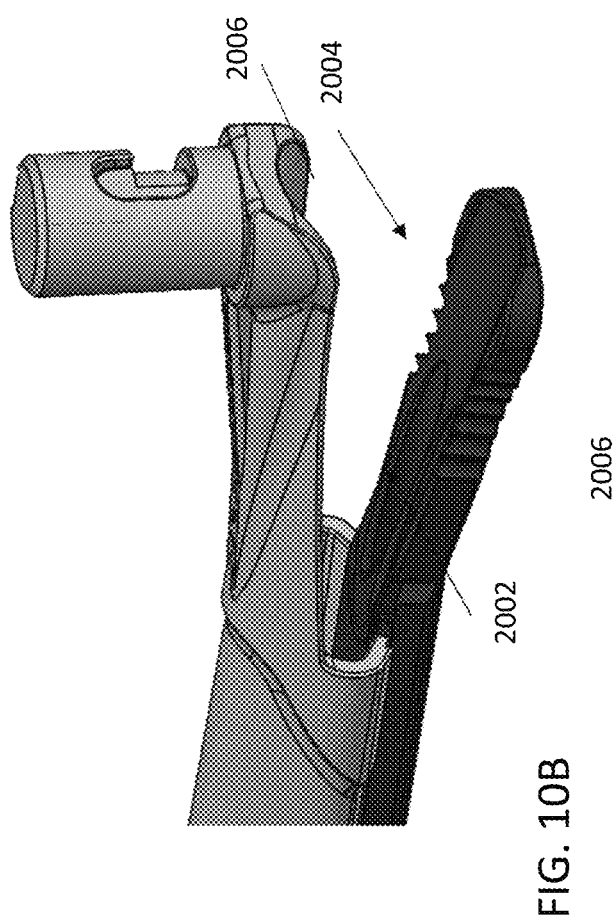
FIG. 10B is a partial perspective view of a proximal portion of the speculum depicted in FIG. 10A.
Figure 10D:
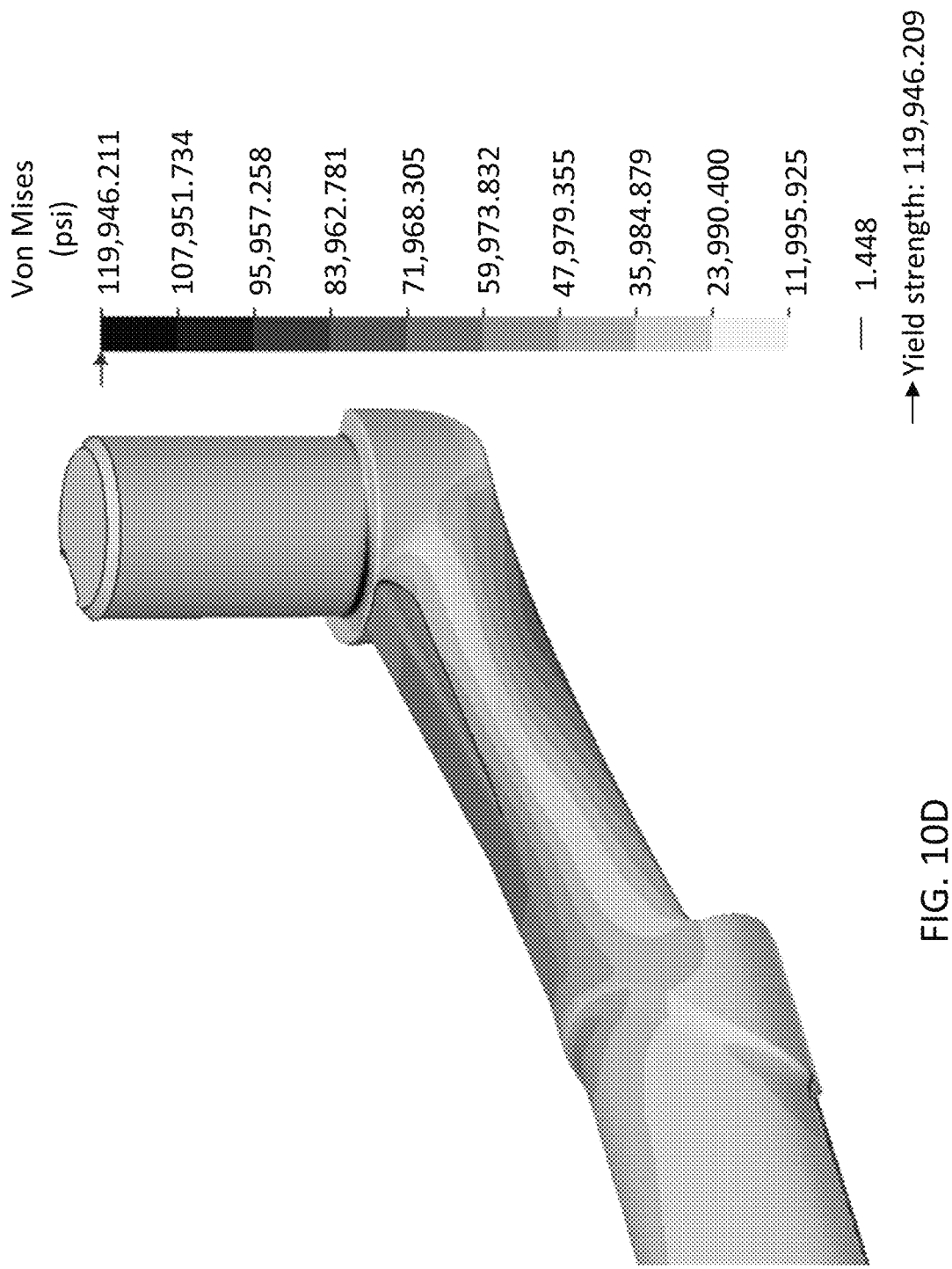
FIG. 10D shows the results of finite element analysis of pressures expected to be experienced by the proximal portion of the speculum depicted in FIG. 10A.

FIG. 10D shows a finite element analysis of pressures experienced by the proximal portion of the speculum 2000 when in use.

The use of 3-D fabrication techniques can be particularly advantageous in providing enhanced structural support in specific areas of the scope, such as the added material discussed above. In particular, 3-D fabrication techniques allow precise and cost effective ways of fabricating different portions of a speculum with different shapes and/or sizes and/or compositions. For example, in this example, the structural reinforcement of the speculum in a region in vicinity of the junction between the top plate and the handle attachment element was achieved by adding additional material to that region to increase its thickness. In other embodiments, such structural reinforcement of certain segments of the speculum can be achieved, for example, by using a different material for forming those segments, e.g., using a different metal.

Figure 11A:
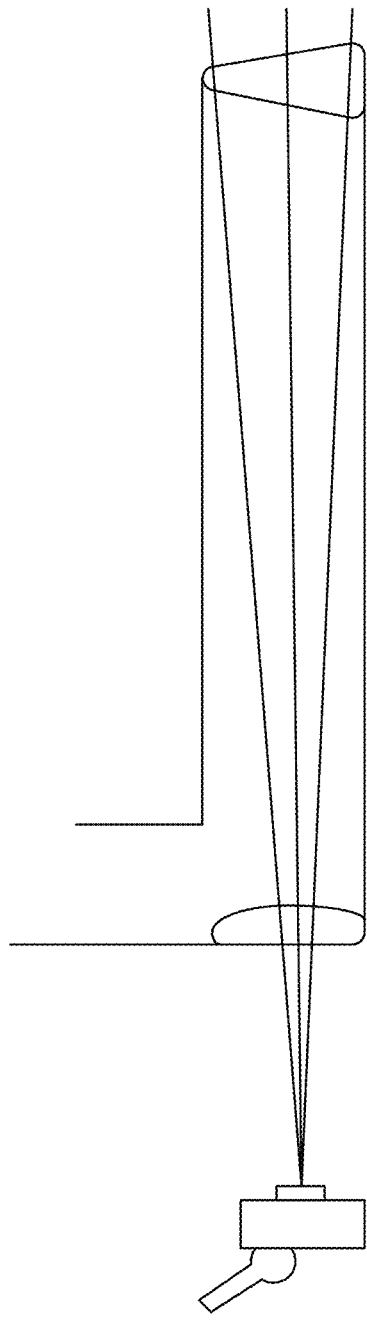
FIGS. 11A and 11B schematically depict two different orientations of a surgical microscope with a front lens that is used to view the larynx through a laryngoscope speculum.
Figure 11B:
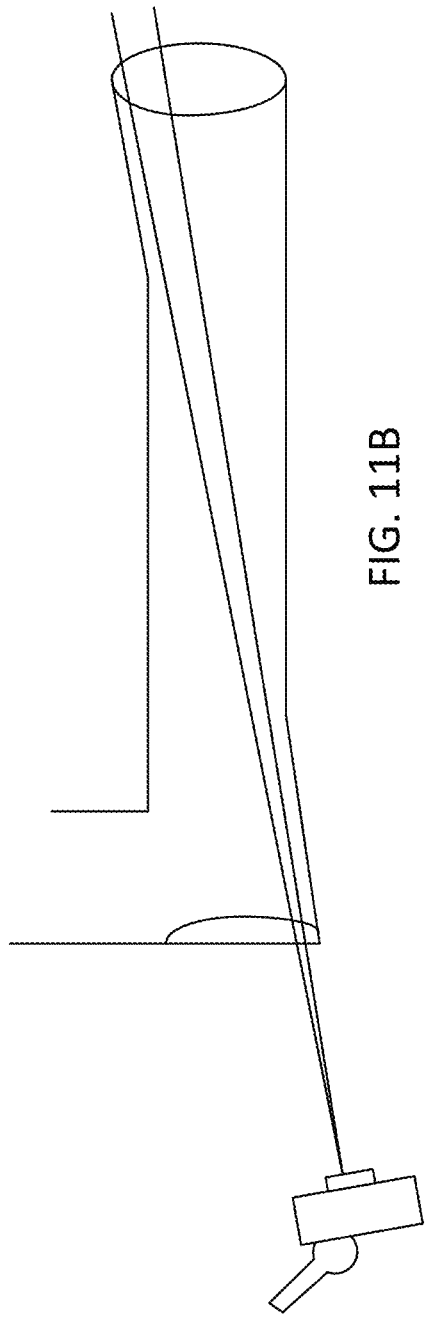

Further, as shown schematically in FIGS. 11A and 11B, a transoral instrument according to the present teachings allows a microscope that is optically coupled to the instrument for viewing a surgical site to be tilted, e.g., up to about 30 degrees relative to the longitudinal axis of the instrument, to allow the surgeon a better visual access to the surgical site.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

Those having ordinary skill in the art will appreciate that various changes can be made to the above embodiments without departing from the scope of the present teachings.

What is claimed is:

1. A method of redesigning a previously-fabricated a laryngoscope, a pharyngoscope, or oral cavity retractor, comprising:
generating a computerized 3-D model of the previously-fabricated laryngoscope, pharyngoscope, or oral cavity retractor, acquiring an anatomical profile of an upper aerodigestive tract of a subject or a respective average anatomical profile of a group of subjects and generating said computerized 3-D model based on any of said anatomical profile of the subject or said average anatomical profile of the group of subjects, wherein any of the anatomical profile of the subject or the average anatomical profile of the group of subjects is based on a plurality of anatomical features including bone structures and associated soft tissues and rheology of one or more soft tissues of the upper aerodigestive tract, utilizing the 3-D model to identify one or more segments or components of the previously-fabricated laryngoscope, pharyngoscope, or oral cavity retractor that require redesign,
adjusting one or more parameters of the 3-D model to obtain a 3-D redesign of said one or more segments or components, and
fabricating said redesigned one or more segments or components based on said 3-D redesign using an additive manufacturing technique.

2. The method of claim 1, wherein said additive manufacturing technique comprises 3-D printing.

3. The method of claim 2, further comprising utilizing any of a metal, a plastic or a composite in said 3D printing.

4. The method of claim 1, further comprising utilizing a structural finite element analysis to identify at least one of said one or more segments or components associated with said 3-D design that require structural reinforcement based on stress and/or strain to which said one or more segments or component are subjected during use.

5. The method of claim 4, wherein said fabricating of said redesigned one or more segments or components comprises structurally configuring said redesigned one or more segments or components so as to provide strengthening and/or structural reinforcement of said one or more segments or components.

6. The method of claim 5, wherein the step of structurally configuring said redesigned one or more segments or components comprises selecting any of a thickness, shape and composition of said redesigned one or more segments or components such that said redesigned one or more segments or components can withstand forces applied thereto during use of said laryngoscope, said pharyngoscope, or said oral cavity retractor.

7. The method of claim 1, wherein said laryngoscope comprises a speculum having a top plate coupled to a base plate and said method includes adjusting at least one of a thickness, shape, and composition of at least a portion of said top plate.

8. The method of claim 1, wherein said 3-D redesign of said one or more segments or components results in a desired visual access to an upper aerodigestive tract of a subject or a group of subjects, wherein said desired visual access is characterized by a maximum tilt of a surgical microscope optically coupled to any of said laryngoscope, said pharyngoscope or said oral cavity retractor relative to a longitudinal axis of any of said laryngoscope, said pharyngoscope or said oral cavity retractor that can be used for viewing a surgical site of interest in the upper aerodigestive tract of a subject or a group of subjects.

9. The method of claim 8, wherein said maximum tilt is about 30 degrees.

10. The method of claim 8, wherein said surgical site of interest comprises an anatomical structure of the upper aerodigestive tract.

11. A method comprising:
generating an anatomical profile of an upper aerodigestive tract associated with a subject or a respective average anatomical profile associated with a group of subjects based on a plurality of anatomical features; wherein the anatomical features include bone structures and associated soft tissues of the upper aerodigestive tract for generating a three-dimensional contour of at least one airway lumen of the upper aerodigestive tract and rheology of one or more soft tissues of the upper aerodigestive tract, wherein the rheology of the one or more soft tissues includes information about distensibility of said soft tissues, and
producing at least one component of a laryngoscope, a pharyngoscope, or an oral cavity retractor based on the anatomical profile.

12. The method of claim 11, wherein the step of generating the anatomical profile comprises utilizing image data of the upper aerodigestive tract.

13. The method of claim 11, wherein any of said anatomical profile associated with a subject and the respective average anatomical profile associated with a group of subjects includes a three-dimensional profile of jaw-opening capacity, aerodigestive lumen, anatomical soft-tissue structural conformation, and bone structures as well as rheology of anatomic soft tissue peripheral to an airway lumen.

14. The method of claim 11, further comprising:
producing said at least one component of the laryngoscope, pharyngoscope, or oral cavity retractor with a three-dimensional (3D) printer.

15. The method of claim 14, where the component comprises a metal, plastic, or composite material.

16. The method of claim 11, further comprising:
determining a material of said at least one component of the laryngoscope based on at least one of the anatomical profiles, structural requirements, ease of maintenance and sterilization, and economy of production.

17. The method of claim 11, wherein the at least one component is a top plate of a speculum.

18. The method of claim 11, wherein the at least one component is a base plate of a speculum.

19. The method of claim 11, further comprising:
determining a parameter of the at least one component based on the anatomical profile of the subject or the average anatomical profile of a group of subjects, and producing the at least one component based on the determined parameter.

20. The method of claim 19, wherein the parameter includes a length of any of a speculum and/or a base plate, an inner diameter of a lumen of the laryngoscope, a radius of curvature of the speculum, or a tilt angle of a proximal portion of the base plate relative to the rest of the base plate.

\* \* \* \* \*